(12) United States Patent
Nielsen et al.

(10) Patent No.: US 10,564,412 B2
(45) Date of Patent: Feb. 18, 2020

(54) TUNABLE FILTER INCLUDING AN ANGULAR DISPERSIVE ELEMENT FOR A BROAD BAND SOURCE

(75) Inventors: Frederik D. Nielsen, Copenhagen (DK); Carsten L. Thomsen, Virum (DK); Weidong Sheng, Snekkersten (DK); Erik B. Thomsen, Slangerup (DK)

(73) Assignee: NKT PHOTONICS A/S, Birkerod (DK)

( * ) Notice: Subject to any disclaimer, the term of this patent is extended or adjusted under 35 U.S.C. 154(b) by 0 days.

(21) Appl. No.: 13/992,784

(22) PCT Filed: Dec. 12, 2011

(86) PCT No.: PCT/DK2011/050475
§ 371 (c)(1),
(2), (4) Date: Aug. 22, 2013

(87) PCT Pub. No.: WO2012/076021
PCT Pub. Date: Jun. 14, 2012

(65) Prior Publication Data
US 2013/0329270 A1    Dec. 12, 2013

Related U.S. Application Data

(60) Provisional application No. 61/422,469, filed on Dec. 13, 2010.

(30) Foreign Application Priority Data

Dec. 10, 2010 (DK) ................................. 2010 01114
Mar. 29, 2011 (DK) ................................. 2011 00227

(51) Int. Cl.
*G02B 26/00* (2006.01)
*G02B 27/00* (2006.01)

(52) U.S. Cl.
CPC ........... *G02B 26/002* (2013.01); *G02B 27/00* (2013.01)

(58) Field of Classification Search
CPC ...... G02F 1/33; G02F 1/35; G01J 3/12; G01J 3/1256; G01J 3/04; G01J 3/1804;
(Continued)

(56) References Cited

U.S. PATENT DOCUMENTS 5,039,855 A    8/1991 Kemeny et al.
5,359,409 A    10/1994 Wildnauer et al.
(Continued)

FOREIGN PATENT DOCUMENTS

DE    10 2007 024 075 A1    11/2008
EP    2 081 074 A1    7/2009
(Continued)

OTHER PUBLICATIONS

Pan et al., "Noninvasive Imaging of Living Human Skin with Dual-Wavelength Optical Coherence Tomography in Two and Three Dimensions", J. Biomed. Opt. 3(4), 446-455 (Oct. 1998).*
(Continued)

*Primary Examiner* — Wen Huang
(74) *Attorney, Agent, or Firm* — Buchanan Ingersoll & Rooney P.C.

(57) ABSTRACT

A fluorescence measurement system comprising a broadband light source and acousto-optical tunable filter (AOTF) controlled by a control unit using an acoustic RF signal provided by a Voltage Controlled Oscillator (VCO).

19 Claims, 12 Drawing Sheets

(58) Field of Classification Search
CPC .... G01N 21/62; G02B 5/202; G02B 21/0056; G02B 21/0064; G01B 11/24; H04J 14/0209; C03B 2203/14
USPC ... 359/226.2, 223.1, 226.1, 197.1, 285, 286, 359/287, 305, 8, 309, 310, 350; 356/451, 356/477

See application file for complete search history.

(56) References Cited

U.S. PATENT DOCUMENTS

| | | | |
|---|---|---|---|
| 5,793,912 A * | 8/1998 | Boord et al. | 385/37 |
| 7,009,763 B1 | 3/2006 | Wolleschensky | |
| 7,787,503 B2 | 8/2010 | Wadsworth | |
| 7,800,818 B2 | 9/2010 | Mattsson | |
| 8,059,333 B2 | 11/2011 | Mattsson | |
| 8,064,128 B2 | 11/2011 | Mattsson et al. | |
| 2002/0057867 A1 * | 5/2002 | Okayama | 385/24 |
| 2004/0105637 A1 | 6/2004 | Goto et al. | |
| 2004/0124366 A1 | 7/2004 | Zeng et al. | |
| 2004/0175082 A1 * | 9/2004 | Birks et al. | 385/123 |
| 2004/0246477 A1 | 12/2004 | Moon et al. | |
| 2007/0133086 A1 | 6/2007 | Wilhelm et al. | |
| 2007/0160325 A1 * | 7/2007 | Son et al. | 385/37 |
| 2007/0188855 A1 | 8/2007 | Shishkov et al. | |
| 2007/0232902 A1 | 10/2007 | Termaura | |
| 2010/0020319 A1 * | 1/2010 | Demos | A61B 5/0075 356/301 |
| 2010/0134867 A1 * | 6/2010 | Gugel et al. | 359/287 |
| 2010/0198397 A1 | 8/2010 | Berghmans | |
| 2010/0254414 A1 | 10/2010 | Bouma et al. | |

FOREIGN PATENT DOCUMENTS

| | | |
|---|---|---|
| JP | 2002156545 | 5/2002 |
| JP | 2007275193 | 10/2007 |
| JP | 2010538278 | 12/2010 |
| WO | 99/04311 A1 | 1/1999 |
| WO | 00/37985 A2 | 6/2000 |
| WO | 2006/113476 A2 | 10/2006 |
| WO | 2009030004 | 3/2009 |
| WO | 2010/108038 A2 | 9/2010 |

OTHER PUBLICATIONS

Dubey et al., "Full-field swept-source optical coherence tomography with Gaussian spectral shaping", Proc. of SPIE vol. 7155, 71551F (2008).*

Farkas, et. al., "Non-invasive image acquisition and advanced processing in optical bioimaging", Computerized Medical Imaging and Graphics 22 (1998) 89-102.*

McConnell, "Noise Analysis of a White-Light Supercontinuum Light Source for Multiple Wavelength Confocal Laser Scanning Fluorescence Microscopy" Journal of Physics D: Applied Physics, (2005), vol. 38, Issue 15, pp. 2620-2624.

G. P. Agrawal, "Fiber-Optic Communication Systems" Second Edition, Wiley Series in Microwave and Optical Engineering, ISBN 0-471-17540-4, pp. 300-302, (5 pages).

International-Type Search Report (Forms PCT/ISA 201 A) dated Jul. 18, 2011, by the European Patent Office in corresponding National Application No. DK 201001114. (4 pages).

Search Report and Opinion dated Jul. 26, 2011, by the Danish Patent and Trademark Office in corresponding Danish Patent Application No. PA 2010 01114. (6 pages).

Search Report and Opinion dated Nov. 11, 2011, by the Danish Patent and Trademark Office in corresponding Danish Patent Application No. PA 2011 00227. (5 pages).

International Search Report (Form PCT/ISA/210) and the Written Opinion of the International Searching Authority (Form PCT/ISA/237) dated Jan. 26, 2012, by the Nordic Patent Institute in corresponding International Application No. PCT/DK2011/050475. (9 pages).

Office Action issued in corresponding Japanese Patent Application No. 2013-542376, dated Aug. 4, 2015. 2 pages.

* cited by examiner

TUNABLE FILTER INCLUDING AN ANGULAR DISPERSIVE ELEMENT FOR A BROAD BAND SOURCE

The invention relates to an optical filter for filtering a broadband beam from a broad band source, e.g. a supercontinuum source.

One object of the present invention is to provide a filter for filtering an incoming broadband beam, the broadband beam defining a beam path through said filter. In one embodiment the filter comprises beam guiding optics, an angular dispersive element, a coupling lens, and an optical waveguide. The beam guiding optics being arranged to guide an incoming broadband beam along a first portion of said beam path. The angular dispersive element being arranged so that said first portion of said broadband beam is incident on said angular dispersive element at an incident angle, whereby light at different wavelengths of the broadband beam are exiting said angular dispersive element in different angles providing an angular dispersed beam. In one embodiment said first portion of the beam is the entire broadband beam and in one embodiment it is a sub-portion (less than 100%) of the broadband beam. The coupling lens is arranged after said angular dispersive element, said lens being arranged to focus said angular dispersed beam to a spot at a first position along the beam path. The optical waveguide comprising a light guiding portion and an end facet arranged at said first position so that the light guiding portion collects at least part of the beam focused into said spot.

In the context of the present invention the phrase "angular dispersive element" is an element which spreads the individual wavelengths in an incoming broad band beam to different output angles. Alternatively it can also combine multiple single wavelength beams with different incoming angles.

In the context of the present invention the phrases "before" and "after" used in relation to the positioning of different parts of the device, the phrase "before the element" is in one embodiment taken to mean a position along the beam path between the entry point of the device and the element, and the phrase "after the element" is in one embodiment taken to mean a position along the beam path between the element and the exit point of the device. In the present context the term device is a generalized term for filter or filter system. In one embodiment a device is a unit or box comprising the filter separate from the light source. In one embodiment the device is a unit or box comprising filter or filter system optically connected to an integrated broadband light source.

In the present context beam guiding optics is optics (bulk or fiber-based) to direct the broadband beam. In one embodiment beam guiding optics is formed by the exit from the broadband light source providing the broadband beam. In one embodiment beam guiding optics is formed by the angular dispersive element alone or in combination with one or more lenses and/or one or more reflective components such as a rotatable mirror.

One object of the invention is to provide a device for modifying an incoming broadband beam, the device comprising a first and a second filter according to the invention. The device comprising a spectral splitter arranged before the filters to split an incoming broadband beam into two beams of which one beam has light at wavelengths in a higher wavelength range and one beam has light at wavelengths in a lower wavelength range, one of the two beams being directed into the first filter and the other one of the two beams being directed into the second filter.

One object of the invention is to provide a tunable broadband filter for modifying the spectral shape of a broadband beam propagating along a beam path, said broadband filter comprising first tunable element and a control unit. In one embodiment, the first tunable element is arranged to suppress light outside one wavelength range of the broadband beam. The control unit is arranged to control arranged to control the first tunable element. In one embodiment the first tunable element is a filter according to any of the embodiment of the invention. In one embodiment the first tunable element comprises a reflective element and an angular dispersive element, wherein said reflective element and/or said angular dispersive element can be rotated such that the angle in which said broadband beam is incident on said spatially dispersive element can be changed and wherein said control unit controls the rotation of the elements. In one embodiment said broadband beam is incident on a first surface of said spatially dispersive element. When the incident angle is changed a shift in the central wavelength of the one wavelength range will in one embodiment occur. In one embodiment the tunable element of said filter comprises a coupling lens and an optical waveguide comprising a light guiding portion and an end facet, the coupling lens being arranged to couple a part of the beam exiting the angular dispersive element into said light guiding portion.

In one embodiment the term control unit refers to circuitry for electronic control in general and need not necessarily be integrated in a single box or device. For example, in one embodiment the system comprises a control unit for controlling a feedback loop comprising a tunable filter having a control unit for controlling the filter. For simplicity reference will be made to a single control unit even though the function of the control unit may be implemented using two or more units.

The spectral shape of the filtered broadband beam is in one embodiment selected from the group of a Gaussian profile, a Lorentzian profile, a Bessel profile, a Voigt profile or a super Gaussian profile.

One object of the invention is to provide a filter for filtering an incoming broadband beam modifying said beam with respect to at least a first parameter, said filter comprising a first tunable element and a control unit. The first tunable element is arranged to modify the broadband beam with respect to said first parameter. The control unit is arrange to provide a control signal to the first tunable element controlling the modification of said broadband beam on a time scale shorter than $t_1$;

One object of the invention is to provide a system for filtering a broadband beam, said system comprising
  a broadband light source providing a broadband beam; and
  a filter according to the present invention, said filter being arranged to filter the beam from a said broadband light source.

One object of the invention is to provide a dual-band OCT (Optical Coherence Tomography) system comprising:
  a broadband light source providing a broadband beam; and
  a device according to the present invention arranged to filter the broadband beam from said broadband light source providing a dual band signal.

One object of the invention is to provide an OCT system comprising:
  a broadband light source providing a broadband beam; and a filter according to the present invention arranged to filter the broadband beam from said broadband light source providing a filtered broadband beam suitable for an OCT system.

One object of the invention relates to the use of a filter according to the present invention for filtering a signal from a broadband source. In this context signal from a broad band source refer to a broadband beam output from the source. The filtered beam exiting the filter is in one embodiment used in relation to a system for Optical Coherence Tomography. The filtered beam exiting the filter is in one embodiment used in relation to a system for white-light interferometry. The filtered beam exiting the filter is in one embodiment used in relation to a system for flow cytometry, spinning disk or hyper spectral applications. In the context of the phrase "used in relation to" refers to use as a light source for the respective system for example an OCT system or a flow cytometer.

One object of the invention relates a system for dividing a broadband beam into one or more sub-beams, said system comprising two or more tunable elements and a controller arranged to control at least two of said tunable elements for separate time intervals; and an RF splitter for splitting the RF signal (control signal) between the tunable elements.

One object of the invention relates a system for dividing a broadband beam into one or more sub-beams, said system comprising two or more tunable elements; a controller arranged to control at least two of said tunable elements for separate time intervals; and a switch for switching the control of the control unit between the two tunable elements.

In one embodiment, the angular dispersed beam in said spot has a larger cross sectional diameter than the cross sectional diameter of the light guiding portion, such that only light in one wavelength range of said incoming angular dispersed beam is collected by said light guiding portion and light at wavelengths outside said one wavelength range is filtered out. The dimension of said spot along which the wavelength of the light in said spot varies is in one embodiment larger than the cross sectional dimension of the light guiding portion along that dimension, such that the spectral width is in one embodiment determined at least in part by the ratio of these dimensions.

In one embodiment the one wavelength range have a spectral shape with a spectral width $\Delta\lambda$ and a central wavelength $\lambda_c$.

The spectral width of a wavelength range is in one embodiment defined by the Full Width Half Max, which is given by the difference between the two wavelengths where the optical power is equal to half of its maximum value.

In one embodiment, the beam guiding optics comprises a reflective element arranged to guide said broadband beam along said first portion of the beam path.

In one embodiment the reflective element comprise a least one mirror. At least one of said mirrors is in one embodiment a dichroic mirror.

In one embodiment, the reflective element and/or the angular dispersive element arranged to be rotatable relative to the portion of the beam path between these elements.

In one embodiment the filter is tunable with respect to the central wavelength. The central wavelength is in one embodiment tuned by moving different parts of the filter.

In one embodiment the spot and the end facet can be moved relative to each other in such a manner that said central wavelength is tuned. The spot defined by focusing the angular dispersive broadband beam exiting the angular dispersive element have light at different wavelengths located at different cross sectional positions in the spot. At one side of the spot light is found at relatively shorter wavelengths while at the opposite side of the spot light with relatively longer wavelengths are found. By moving said wave guiding portion and said spot relative to each other, the central wavelength of the spectrum collected and guided by the light guiding portion can be tuned. This is especially true when the cross sectional dimension of said light guiding portion is smaller than the cross sectional dimension of the spot.

In one embodiment, the distance between the coupling lens and the fiber end facet can be changed such that the cross sectional dimension of the spot at said fiber end facet changes and the spectral width of the filtered broadband beam is tuned.

In one embodiment, the incident angle of said first portion of said beam path relative to said angular dispersive element can be changed such that said central wavelength is tuned. The incident angle is in one embodiment changed by rotating said angular dispersive element relative to said first portion of said beam path. The reflective element is in one embodiment arranged to be rotatable such that the first portion of said beam path is changed and such that said incident angle changes.

In one embodiment, the filter comprises a control unit arranged to control the relative orientation of the angular dispersive element and the beam guiding optics.

The spectral width of the filtered broadband beam is in one embodiment in the range of about 10 nm to about 1000 nm, such as in the range of about 20 nm to about 700 nm, such as in the range of about 30 nm to about 500 nm, such as in the range of about 50 nm to about 400 nm, The central wavelength of the filtered broadband beam is in one embodiment in the range of about 400 nm to about 2000 nm, such as in the range of about 500 nm to about 1500 nm. The central wavelength is in one embodiment in the range of about 500 nm to about 700 nm, or in the range of about 700 nm to about 900 nm, or in the range of about 900 nm to about 1100 nm, or in the range of about 1300 nm to about 1400 nm.

In one embodiment, the largest cross sectional diameter of the light guiding portion is smaller than the largest cross sectional diameter of the spot, the spectral width being determined by the ratio of the cross sectional diameters/areas of the light guiding portion and the spot.

The angular dispersive element is in one embodiment selected from the group of a wedge, or a prism and a diffractive element.

A wedge may be arranged to disperse light incident on the wedge such that light at different wavelengths is dispersed in different directions when exiting said wedge. In one embodiment this angular dispersion occurs at the first and/or second surface of the wedge traversed by the incident light.

In one embodiment the optical waveguide comprises an optical fiber, such as a single-mode optical fiber, such as a microstructured endlessly single-mode optical fiber.

In one embodiment a spatial filter element is arranged in said beam path, preferably between the angular dispersive element and said coupling lens.

The spectral shape of the filtered broadband beam is in one embodiment selected from the group of a Gaussian profile, a Lorentzian profile, a Bessel profile, a Voigt profile or a super Gaussian profile.

In one embodiment, the filter comprises a monitoring unit arranged to monitor said beam at a monitor position along the beam path. The monitor position is in one embodiment after said optical waveguide. In one embodiment the filter comprise a reflector for directing a fraction of the optical power of the beam into said monitoring unit. This reflector is in one embodiment a surface of an optical element such as the focusing lens. This has the advantage that a separate optical element obtaining a fraction of the beam is not required. In one embodiment the monitor unit measures a spectral characteristic of the beam and/or the monitor unit measures the optical power in the beam.

In one embodiment the monitoring unit comprises a spectrometer allowing measurement of the distribution of the optical fiber at the different wavelengths. For some applications it is sufficient to monitor the optical power at a single wavelength and the monitoring unit may in one embodiment consist of a simple optical power measuring unit, such as based on direct measurement from a photodiode.

In one embodiment, the monitor is arranged to provide a feedback to said control unit. The control unit is in one embodiment arranged to control the relative orientation of said first portion of said beam path and said angular dispersive element based on said feedback in such a manner as to stabilize said filtered broadband beam. The filtered broadband beam is in one embodiment stabilized with respect to the spectral profile and/or with respect to the optical power of the beam. An LCD (Liquid Crystal Display) or a DLP (Digital Light Processing) filter may also be employed to provide adjustable filtering which may be suitable for a feedback loop. In one embodiment an LCD or a DLP is applied as a tunable dampening and/or tunable spatial filter (see e.g. features 52, 53, 62 and 63 of FIG. 5*a* and FIG. 6).

In the context of the present invention, the phrase stabilized refers in one embodiment to the situation wherein the change in a parameter of the beam, such as the optical power in the beam of the spectral shape of the beam, is smaller than a given maximum value within a given period of time. The period of time is in one embodiment a fraction of a second, such as 0.001 s, 0.01 s, or 0.1 s, a second, or several seconds such as 5 s, 10 s, or 60 s. The change in the parameter of the beam is in one embodiment an absolute change or a relative change, such as a change which is less than some percentage of the value of the parameter, such as less than about 30%, such as less than about 20%, such as less than about 10%, such as less than about 5%, such as less than about 2%, such as less than about 1%, such as less than about 0.1%.

In one embodiment, the filtered broadband beam is stabilized in less than about 1 s, such as less than about 0.5 s, such as less than about 0.1 s, such as less than about 0.05 s, such as less than about 0.01 s, such as less than about 0.005 s, such as less than about 0.001 s, such as less than about 0.1 ms.

In one embodiment, the filter comprises a spectral splitter arranged before the reflective element, said spectral splitter is arranged to split an incoming broadband beam into one beam with light having wavelengths in a higher wavelength range and one beam with light having wavelengths in a lower wavelength range. The spectral splitter is in one embodiment a dichroic mirror or a linear variable filter.

In one embodiment, the device comprises a spectral combiner arranged to combine the filtered beams exiting from the first and the second filters of the device. In one embodiment the combiner comprises a dichroic mirror, a linear variable filter or a wavelength division multiplexer arranged to combine the filtered beams exiting from the first and second filters.

In one embodiment the device is arranged to filter an incoming broadband beam to provide a signal for dual-band OCT systems.

In one embodiment, the filter and/or the device comprise an entry point through which a beam from a light source can enter the filter or the device.

In one embodiment, the filter and/or the device comprise an exit point through which the filtered broadband beam can exit the filter or the device.

In one embodiment, the first tunable element comprises an element is arranged to of change its refractive index in response to a stimulus. The stimulus is in one embodiment an acoustic signal or an electrical signal.

In a filter wherein said stimulus is an electrical signal said first tunable element comprise in one embodiment an electro-optic tunable filter.

In one embodiment of a filter wherein said stimulus is an acoustic signal said first tunable element comprises an acousto-optic tunable filter (AOTF). The AOTF is in one embodiment driven by a Radio Frequency (RF) oscillator.

In one embodiment, the filter comprises a second tunable element also referred to as tunable filter. In one embodiment, the filter comprises a third tunable element and optionally a fourth tunable element. In one embodiment, the filters of the second and subsequent tunable elements are substantially identical to the first tunable element. In one embodiment one or more of the second and subsequent tunable elements are adapted to filter/pass different wavelength ranges relative to the first tunable element and/or each other. In one such embodiment the first tunable element has a limited bandwidth, e.g. an AOTF substantially limited to visible wavelengths. A second tunable filter may therefore be employed to filter longer wavelengths outside the bandwidth of the first tunable filter.

In one embodiment the filter comprises a Fabry Perot resonator, such as a FFP (Fiber Fabry Perot), or a thin film filter, a thin film (Varia type), or a monochromator type filter.

In one embodiment, the filter comprises a spectral splitter arranged before the first tunable element, said spectral splitter being arranged to split an incoming broadband beam into one beam with light having wavelengths in a higher wavelength range and one beam with light having wavelengths in a lower wavelength range.

In one embodiment, the filter comprises a polarization beam splitter arranged before the first tunable element, said polarization beam splitter arranged to split a broadband beam incident on the polarization beam splitter into one beam having a first polarization and one beam having a second polarization.

In one embodiment, the beam having a first polarization and the beam having a second polarization are directed into the same tunable element.

In one embodiment, the beam has a first polarization being directed into one tunable element and said beam having a second polarization being directed into another tunable element.

In one embodiment, the spectral splitter is arranged before two of said polarization splitters such that said incoming broadband beam is split into a first beam and a second beam by said spectral splitter and each of the first and the second beams subsequently are divided into two beams of different polarization, thus generating four beams.

The generated four beams are in one embodiment guided through four different tunable elements. Each of said four different tunable elements is in one embodiment controlled by one or more of said control units.

In one embodiment, the beams generated by splitting the incoming broadband beam are combined again after said tunable filters to provide the filtered broadband beam. A polarization beam splitter is in one embodiment used to combine the split beams.

In one embodiment, the filter comprises at least a first half-wave plate arranged after said polarization beam splitter to rotate the polarization of the one beam having a first polarization and/or the one beam having a second polarization.

The half-wave plate is in one embodiment arranged before a tunable element. In one embodiment, a second half wave plate is arranged after a tunable element.

In one embodiment the first and the second tunable elements are rotated relative to each other, such that the first allows light with one polarization to pass and the second allows the perpendicular polarization to pass.

In one embodiment the control signal provided to the first and second tunable elements is such that said they transmit the same wavelength range, whence the power in said range is increased. In one embodiment this is particularly and advantage for a broadband light source providing shorter wavelengths, such as below 500 nm, such a below 450 nm, such as below 425 nm, such as below 400 nm. In one such embodiment, increasing of power by way of the filter is particularly an advantage for a supercontinuum light source comprising a pump laser (optionally also comprising one or more amplifiers after the pump laser cavity to increase the optical pump power) and a non-linear medium such as an optical fiber. The optical fiber is typically a microstructured optical fiber with a core of substantially pure silica glass optionally comprising one or more voids. It is also possible that the pure silica glass is doped e.g. by Germanium. In one embodiment the fiber is a non-linear fiber. In one embodiment the super continuum light source is a light source according to the inventions of one more of the following U.S. Pat. Nos. 7,800,818, 8,059,333, 7,787,503 and 8,064,128. In one embodiment the supercontinuum light source is a light source according to one or more of the claims of these patents. In one embodiment the increasing of power is advantageous for shorter wavelengths when the wavelength of the pump light is relative long, such as longer than or equal to 800 nm, such as longer than or equal to 950, such as longer than or equal to 980 nm, such as longer than or equal to 1000 nm, such as longer than or equal to 1055 nm, such as longer than or equal to 1100 nm, such as longer than or equal to 1200 nm, such as longer than or equal to 1250 nm. In one embodiment increasing of optical by way of the filter is particularly an advantage for long wavelengths produced by the broadband light source, such as wavelengths longer than or equal to 1800 nm, such as longer than or equal to 1900 nm, longer than or equal to 2000 nm, such as longer than or equal to 2100 nm, such as longer than or equal to 2200 nm such as longer than or equal to 2220 nm. In one embodiment such long wavelengths are difficult to produce with high power in silica based fibers because silica often has a high absorption band in this range. In one embodiment this is particularly true when the pump wavelength is less then 1300 nm, such as less than 1200 nm, such as less than 1100 nm. In one embodiment the supercontinuum light source mentioned above is arranged to produce the mentioned short wavelengths as well as the mentioned long wavelengths.

In devices comprising a tunable filter that has a significant loss for one polarization, such as an acousto-optic filter, an otherwise un-polarized beam from a broad band source is in one embodiment polarized and a large fraction of the optical power lost. This is in one embodiment overcome by splitting the incoming beam into a first polarization and a second polarization using e.g. a polarization beam splitter and subsequently directing the first polarization into a first tunable filter.

In one embodiment, the said polarization beam splitter, said half-wave plate and said mirror are combined in an integrated element. In one embodiment this has the advantage of providing a robust and easy to use configuration wherein less manual alignment of the components is required when using the filter.

In one embodiment, the first and second tunable elements are a first and a second AOTF, and said control unit provides a first RF signal said first AOTF and a second RF signal said second AOTF.

In one embodiment individual control of the first and second RF signals provides a combined output with a broader wavelength range than what is possible for the individual filters.

In one embodiment the individual control of the first and second RF signals provides a method for fast polarization switching of the output. This might be realized by alternately turning the two tunable filters on and off in such a manner that they are out of phase.

Designs of AOTFs are well-known in the art. The filter function of an AOTF is at least partly determined by the RF control signal which creates a sound wave in the filter which in turn diffract light with a resonant wavelength into a first order beam and a minus first order beam, each having a new direction compared to the original beam. Typically an AOTF for filtering light from a broad band light source utilizes an RF signal from a Direct Digital Synthesizer (DDS) as a control signal due to properties such as versatility, stability and ease of use in relation to outputting multiple wavelengths. Accordingly, in one embodiment the tunable filter(s) of the present text are formed by an AOTF controlled by an RF signal from a DDS. The However, the inventors have found that for some applications of AOTFs for filtering broad band beams it is preferable to apply a voltage controlled oscillator (VCO) to provide the control signal. Accordingly, in one embodiment, the tunable filter comprises an AOTF where the filter function of the AOTF is controlled by a RF signal provided by a Voltage Controlled Oscillator. In one embodiment the tunable filter(s) of the present text are formed by an AOTF controlled by an RF signal from a VCO. Compared to the DDS a VCO may be arranged to have lower noise. The noise in the RF signal also contributes to the filter function of the AOTF which in one embodiment influences the out-of-band suppression of the AOTF.

One example of applications where out-of-band suppression is a concern is applications where fluorescence is measured from a sample in response to illuminating the sample with light filtered by the AOTF (the sample may in principle also be illuminated with other light as well). Such systems include, but are not limited to a fluorescence microscope, an epifluorescence microscope, a STED microscope, a 4 pi microscope, a SPDM localization microscope, a SMI microscope, a Vertico SMI microscope, fluorescence imaging and a Fluorescence Lifetime Imaging Microscope (FLIM). In particular systems comprising a photon-counter arranged to measure the fluorescent response will benefit from the application of a VCO. The fluorescent response, i.e. light emitted from the sample, is typically emitted at another wavelength than the illumination light. Illumination light at the same wavelength as the fluorescence response may contribute to the noise floor for the measurement of the fluorescent light and thus in turn hinder detection of (the commonly) weak fluorescent response. In one embodiment the output of a broadband light source has a significant spectral density in the wavelength range of the fluorescent response. It is therefore in such an embodiment preferable or even required that the tunable filter arranged to select the light from the broadband light source that illuminates the sample has a high out-of-band suppression. Accordingly, in one embodiment the invention relates to a fluorescence measurement system comprising a. a broadband light source arranged to provide a broadband beam,
b. a first tunable element arranged to filter at least a portion of said broadband beam thereby providing filtered light;
c. a control unit arranged to provide a control signal to said first tunable element;

wherein said first tunable element is an acousto-optic filter (AOTF) and said control signal to said AOTF is an acoustic RF signal provided by a Voltage Controlled Oscillator (VCO) arranged so said AOTF provide an out-of-band suppression of more than or equal to 25 dB, such as more than or equal to 30 dB, such as more than or equal to 35 dB, such as more than or equal to 40 dB, such as more than or equal to 45 dB, such as more than or equal to 50 dB, such as more than or equal to 55 dB, such as more than or equal to 60 dB. Preferably, the AOTF and VCO is in one embodiment arranged to provide an out-of-band suppression of more than or equal to 35 dB and even more preferably more than or equal to 40 dB, and even more preferably more than or equal to 45 dB, and even more preferably more than or equal to 50 dB, and even more preferably more or equal to 55 dB, and even more preferably more or equal to 60 dB. In one embodiment the fluorescence measurement system is arranged to d. Illuminate a sample with light filtered by said AOTF and
e. measure a fluorescent response to said illumination from said sample in a wavelength range in which said AOTF provides said out-of-band suppression.

As discussed below, one typical family of fluorescent dyes have a spacing between the illumination wavelength and emission ranging from about 10 nm to above 100 nm, but it is possible that the distance is shorter or longer. Accordingly, in one embodiment the AOTF provides the out-of-band suppression in a wavelength range extending from 1 nm from the illumination wavelength or more, such as more than 5 nm from the illumination wavelength or more, such as more than 10 nm from the illumination wavelength or more, such as more than 15 nm from the illumination wavelength or more, such as more than 20 nm from the illumination wavelength or more, such as more than 30 nm from the illumination wavelength or more, such as more than 40 nm from the illumination wavelength or more. In one embodiment this out-of-band suppression has an upper limit such as 500 nm from the illumination wavelength or less, such as 200 nm or less, such as 150 nm or less, such as 100 nm or less, such 75 nm or less, such as 50 nm or less, such as 25 nm or less.

In one embodiment the AOTF is arranged so that the beam path of the diffracted beam is independent of the RF frequency being applied to said AOTF.

In one embodiment the fluorescent measurement system is arranged to measure said fluorescent response as a function of time. In one embodiment such systems will benefit from the application of the VCO due to a higher sensitive to noise because of the short measurement time.

In one embodiment RF-signals from multiple VCOs are multiplexed into a control signal so that allow the AOTF to output multiple spectral lines in said filtered light. Out-of-band suppression as defined below is in this case defined as suppression of light in wavelengths away from the multiple spectral lines.

The control signal to an AOTF is typically substantially a single frequency (the main frequency) signal for each wavelength to be diffracted by the AOTF. Each wavelength typically defines as band of wavelengths (see e.g. peak "A" of FIG. 20) but is referred to as a single wavelength. Noise and sidebands in the control signal will typically lead to the deflection of wavelengths outside side the main band (e.g. peak A), i.e. reduction of the out-of-band suppression. In one embodiment the control signal to the AOTF is in a range of 10 MHz to 500 MHz, such as in a range of 25 MHz to 300 MHz, such as in a range of 25 MHz to 200 MHz. In one embodiment the control signal to a single AOTF is tunable with a sub-band of the mention ranges, such as a sub-band narrower than or equal to 100 MHz, such as a sub-band narrower than or equal to 80 MHz, such as a sub-band narrower than or equal to 60 MHz, such as a sub-band narrower than or equal to 50 MHz, such as a sub-band narrower than or equal to 40 MHz, such as a sub-band narrower than or equal to 30 MHz, such as a sub-band narrower than or equal to 20 MHz, such as a sub-band narrower than or equal to 10 MHz. In one embodiment the control signal to a single AOTF is tunable with a sub-band of the mention ranges, such as a sub-band of at least 10 MHz, such as a sub-band of at least 20 MHz, such as a sub-band of at least 40 MHz, such as a sub-band of at least 60 MHz, such as a sub-band of at least 80 MHz, such as a sub-band of at least 100 MHz. In one embodiment a narrower range corresponds to a lower out-of-band noise. In one embodiment out-of-band suppression of the AOTF is improved by applying a VCO with a relatively high oscillation frequency and subsequently sub-divide this frequency to a frequency suitable for the AOTF. Accordingly, in embodiment the VCO oscillates at a frequency of more than or equal two times the frequency of the control signal to the AOTF, such as more than or equal to 4 times, such as more than or equal to 8 times, such as more than or equal to 16 times. However, in one embodiment the control signal has the same main frequency as the VCO. In one embodiment sub-division of the oscillation frequency has the effect that out-of-band phase noise, i.e. phase noise at frequencies away from the main frequency of the control signal, is reduced.

Out of band suppression in fluorescence measurement is typically in the order of about 20 nm away from the illumination wavelengths. Consider for example the Alexa Fluor family of fluorescent dyes where the spacing between absorption wavelength (i.e. the illumination wavelength) and the emission wavelength ranges from about 10 nm to over 100 nm, but is typically in the order of 20 nm. In one embodiment this corresponds to a change in the range of 1 MHz to 50 MHz in the control signal to the AOTF. As the out-of-band-suppression is particularly required at the emission wavelength the out-of-band suppression of the control signal is therefore in one embodiment determined as the noise density measured at a frequency of more than 1 MHz relative to the main frequency, such as more than or equal to 2 MHz relative to the main frequency, such as more than or equal to 3 MHz relative to the main frequency, such as more than or equal to 4 MHz relative to the main frequency, such as more than or equal to 5 MHz relative to the main frequency, such as more than or equal to 7 MHz relative to the main frequency, such as more than or equal to 10 MHz relative to the main frequency, such as more than or equal to 20 MHz relative to the main frequency. In one embodiment the out-of-band suppression of the AOTF scales substantially linearly with the out-of-band suppression of the control signal, at least when issue such as cross-talk in the AOTF are disregard. Accordingly, in one embodiment the control signal has an out-of-band suppression of more than or equal to that of the AOTF. In one embodiment the control unit comprises an amplifier arranged to amplify the RF signal from the source (e.g. DDS or VCO) before it is transmitted to the AOTF. This amplifier will typically add noise to the signal. Accordingly, in one embodiment the VCO has an out-of-band suppression of more than or equal to that of the control signal, such as 3 dB more than the control signal or more, such as 6 dB or more, such as 9 dB or more, such as 12 dB or more, such as 15 dB or more, such as 18 dB or more.

For some applications it is important to control the output wavelength and a VCO may in one embodiment be more prone to drift compared to a DDS. In one embodiment a VCO controlled AOTF as discussed above is implement along with a feedback system according to any of the embodiments described in this text to stabilize the AOTF output, for example a feedback system as laid out in FIG. 7. In one embodiment it is an advantage locking the VCO and utilizing fixed frequency steps. In one embodiment stabilization is further or alternatively provided by LCD or DLP filter applied as a tunable dampening and/or tunable spatial filter for example as part of a feedback loop. In one embodiment, two beams generated either by spectral splitters or polarization beam splitters are guided through one tunable element. This may be advantageous when it is intended that the two beams are filtered by the same filter function.

In one embodiment, the filter comprises a monitoring unit arranged to monitor said beam at a monitor position along the beam path. The monitor position is in one embodiment after said tunable element and/or after said angular dispersive element. In one embodiment, the filter comprises a reflector for directing a fraction of the optical power into said monitoring unit.

In one embodiment the monitor unit measures the optical power in the beam and/or a spectral characteristic of the beam. In one embodiment, the monitor unit provides individual measurements of the optical power at a number N of wavelengths of the beam. The number N is in one embodiment 2 or more, such as 3, 4, 5, 6, 7, 8, 9, 10, 12, 16, 20 or more.

In one embodiment, the monitor is arranged to provide a feedback to said control unit. The control unit is in one embodiment arranged to control the tunable element based on said feedback in such a manner as to stabilizing the filtered beam exiting the filter. The filtered beam is in one embodiment stabilized with respect to the spectral profile. In one embodiment, the filtered beam is stabilized with respect to the optical power in several of said N wavelengths. In one embodiment feedback is further or alternatively provided via an LCD or DLP applied as a tunable dampening and/or tunable spatial filter.

In one embodiment, the filtered beam is stabilized with respect to the optical power in the filtered beam.

In one embodiment, $t_1$ is below about 10 milliseconds, such as below about 1 millisecond, such as below 0.1 milliseconds, such as below 0.01 milliseconds, such as below 0.001 milliseconds.

The first parameter is in one embodiment selected from the group of the spectral width, the spectral shape, which is in one embodiment the distribution of optical power over the spectral width, the optical power of the broadband beam, stability of the optical power, the polarization, and the number of peaks in the broadband beam.

A tunable filter, such as an AOTF or band-pass filter formed using linear variable filters, has a filter function where one or more bands or lines of wavelengths pass the filter substantially without loss relative to wavelengths outside these bands or lines. In the present contest loss refers to light lost from the beam path typically either absorbed or reflected away from the beam path. Each band or line has spectral width $\Delta\lambda$, a central wavelength $\lambda_c$ a center wavelength and a wavelength of minimum loss. Often $\lambda_c$ and the wavelength of minimum loss are substantially coinciding, or in the case of a top-hat shaped filter function, a range of wavelengths have substantially the same loss as the wavelength of minimum loss. The filter function further has a full-width-half-maximum (FWHM) bandwidth defining the pass-band of the filter function. As noted above, out-of-band suppression is in one embodiment of concern in applications where fluorescence is measured from a sample in response to illuminating the sample with light filtered by the tunable filter. In one such embodiment out-of-band suppression (or just suppression) is the minimum loss of the filter in the wavelength range of the fluorescent response to be measured relative to the minimum loss in the pass band of the filter.

In one embodiment out-of-band suppression is defined as the minimum loss for wavelengths more than x nm away from the pass band. In one embodiment x equal to 0.5 times the FWHM bandwidth or more, such as 1 times or more, such as 1.5 times or more, such as 2 times or more, such as 3 times or more, such as 3.5 times or more. In one embodiment x is in one embodiment 5 nm or more, such as 10 nm or more, such as 15 or more, such as more, such as 20 nm or more. In one embodiment the filter has and overall bandwidth of use outside which light is allowed to pass. Therefore, out-of-band suppression is in one embodiment evaluated inside this bandwidth of use. In one embodiment, the bandwidth of use extends up to 50 nm from the center bandwidth of the filter or more, such as up to 100 nm or more, such as up to 200 nm or more, such as up to 300 nm or more, such as up to 400 nm or more, such as up 500 nm or more.

In one embodiment the filter function has a center peak with low loss and a series of side peaks having higher loss. An AOTF is an example of a filter which may exhibit such a filter function. FIG. 20 shows an exemplary filter function of an AOTF with a main transmission peak designated A having a minimum loss at about 640 nm and side peaks B to G. In one embodiment out-of-band suppression is defined as the height of a first side peak (i.e. B or C) relative to the minimum loss of peak A. In one embodiment out-of-band suppression is defined as the height of a second side peak (i.e. D or E) relative to the minimum loss of peak A. In one embodiment out-of-band suppression is defined as the height of a third side peak (i.e. F or G) relative to the minimum loss of peak A. In one embodiment the filter has a top-hat filter function, such as e.g. filter function C in FIG. 16. In one such embodiment out-of-band suppression is defined as the average top-hat plateau (i.e. from about 570 nm to 650 nm for function C of FIG. 16) relative to average loss away from the filter (i.e. wavelengths below about 550 nm and above 670 nm for function C of FIG. 16).

In one embodiment out-of-band suppression is improved by applying multiple filters after each other in place of a tunable filter. Accordingly, in one embodiment said tunable filter comprises two tunable filters. In one embodiment the filter function of these two filters are substantially identical, such as within 10%, in the pass band of the filter. In one embodiment the two tunable filters are two AOTF where one AOTF is arranged to filter filtered light from the other. In this way the out-of-band suppression may be doubled (in dB). In one embodiment the RF-control signal is substantially the same to the two (or more) AOTFs. In one embodiment the RF-control signal is divided from a single VCO or DDS. In one embodiment multiple sources of the RF-signal are applied. In one embodiment the two (or more) AOTFs are calibrated to provide substantially the same filter function. In one embodiment the RF-control signal may therefore be different if the AOTF filter is different e.g. due to production differences. Similarly, in one embodiment two band-pass filters may be applied. In one embodiment multiple filters of different types may be combined. For example an AOTF in combination with a band-pass filter. The AOTF may as an example provide a relatively narrow center peak which can then be tuned inside the pass band of a band-pass filter which has high out-of-band suppression.

As noted above, a filter may have a band of operation outside which the filter as low loss. In one embodiment multiple filters are applied in order to widen the band of operation. For example a band-pass filter (as discussed below) may have a filter function similar to that FIG. 16 curve C. However above (and/or below) certain wavelengths (not shown) loss may reduced again. In one embodiment a further low-pass filter (also referred to as a short-wave pass filter) with a suitable cut-off wavelength is applied to filter wavelengths above these certain wavelengths. Similarly a high-pass filter (also referred to as a long-wave pass filter) may be applied for low wavelengths outside the band of operation of the band-pass filter.

In one embodiment, the control unit is arranged to provide a control signal to said tunable element which varies in time such that said central wavelength is scanned though a part of the wavelength range of said incoming broadband beam.

The tunable element is in one embodiment an AOTF and said control unit is in one embodiment arranged to provide a RF signal to said AOTF (e.g. via a DDS and/or VCO) where the frequency of the RF signal varies in time such that said central wavelength is scanned though a part of the wavelength range of said incoming broadband beam.

The tunable element is in one embodiment an AOTF and said control unit is arranged to provide a RF signal to said AOTF where the frequency or the amplitude of the RF signal varies in time such that the spectral width varies in time.

The broad band light source is in one embodiment selected from the group of a Supercontinuum source, a white light source, a SLED, an active element based ASE source, such as an Erbium based ASE source, a lamp, and a femto second laser.

In one embodiment a broadband beam is an optical beam having power spectrum spanning over at least one octave with at least 10 µW/nm. In one embodiment the broadband beam spans over at least one octave with at least 50 µW/nm, such as more than or equal to 500 µW/nm, such as more than or equal to 1 mW/nm, such as more than or equal to 5 mW/nm, such as more than or equal to 10 mW/nm. In one embodiment broadband beam spans over more than or equal to 0.5 octave, such more than or equal to 1.5 octave, such more than or equal to 2 octaves. In one embodiment a broadband beams is an optical beam having power spectrum spanning over at least one octave measured as full width half maximum (FWHM). In one embodiment the broadband is provided via pumping a non-linear optical element (e.g. a fiber) with pump light. In one embodiment FWHM is determined after subtracting the power spectrum of residual pump light from the power spectrum. In one embodiment a broadband beam is an optical beam having power spectrum S hawing a width $w_S$ so that $w_S \geq 50$ nm, such as $w_S \geq 100$ nm, such as $w_S \geq 200$ nm, such as $w_S \geq 300$ nm, such as $w_S 400$ nm, such as $w_S \geq 500$ nm, such as $w_S \geq 1000$ nm, such as $w_S \geq 1500$ nm, such as $w_S \geq 2000$ nm, such as $w_S \geq 2500$ nm. In one such embodiment the $w_S$ is measured as FWHM. In one embodiment FWHM is determined after subtracting the power spectrum of residual pump light from the power spectrum. In one embodiment a broadband beam may exhibit a power spectrum with one or more holes, so that in one embodiment the span or width of the spectrum is measured as the widest span of wavelengths where the power spectrum exhibits a optical power above the above cited thresholds. For example, one embodiment the power spectrum comprises two peaks spaced 2000 nm apart each above 10 µW/nm, in which case the width or span is determined to 2000 nm. However, in one embodiment the spectrum is a substantially continuous spectrum, so that within the span or width the power spectrum is above the above cited threshold for more than 30% of the width or span, such as more than 50%, such as more than 70%, such as more than 80%, such as more than 90%, such as more than 95%, such as more than 99%, such as 100%.

In one embodiment the broadband light source of the present text is a super continuum light source according to the inventions of one more of the following U.S. Pat. Nos. 7,800,818, 8,059,333, 7,787,503 and 8,064,128. In one embodiment the supercontinuum light source is a light source according to one or more of the claims of these patents.

In one embodiment, the tunable elements each comprise an acousto-optic tunable filter (AOTF), said control unit comprising a RF driver (e.g. DDS and/or VCO) and said switch comprising a RF switch.

In one embodiment, the system further comprises a sensing unit arranged to sense which acousto-optic tunable element is connected to the RF driver. In one embodiment the sensing unit comprises a detector arranged to detect a DC signal at least DC relative to the RF signal. Alternative a high frequency signal outside the band of the RF signal is in one embodiment used.

AOTF crystals of different types have different relations between the RF drive frequency and the filtered wavelength (the diffracted wavelength). It is an advantage to known this relationship in order to improve the absolute wavelength accuracy. Even crystals of the same type can have slightly different drive frequency to diffraction wavelength relationships. Differences can be caused by batch variations, the angle of incidence on the crystal as well as the crystal temperature.

The RF drive frequency to wavelength relationship is often affected by crystal temperature. This relationship can be locked by temperature stabilization of the crystal. Alternatively the influence of crystal temperature can be mapped and compensated e.g. via a look-up table.

Factors like impedance in the RF chain (driver, transmission line and crystal), and RF power/diffraction efficiency linearity have an influence on the RF power needed to reach the highest diffraction efficiency for a specific RF drive frequency/wavelength—this is called optimum RF power. Optimum RF power is a function of RF frequency. In one embodiment this can be mapped and remains constant for that particular combination of components. If any components are replaced—even by an equivalent component—this relationship might be affected. So in order to reach the optimum diffraction efficiency for a specific system the optimum RF power as a function of RF frequency should in one embodiment be mapped as a part of the parameter set.

Knowing the optimum parameter set for a particular crystal is also an advantage when using multiple crystals in a system, either simultaneously or interchangeably (e.g. using an RF switch as described below, or simply by changing the RF cable from one crystal to another).

In one embodiment the crystal parameters can be saved in the AOTF modules—but if a module contains two or more crystals and is controlled by a single RF driver (one at a time, by routing the RF signal to either of the crystals), then it is an advantage if the control unit can determine which of the crystals that is connected.

One way of knowing this is by feeding this information into the system manually. Another way is by sensing which crystal that is connected. By adding an additional signal to the RF transmission line it is possible to determine which crystal is connected. In one embodiment the suitable operating parameters of an AOTF crystal is stored in a memory In one possible implementation, the sensing signal could be a DC bias potential on the RF transmission line. A DC potential can be added and detected without influencing the RF driver or the crystal.

In one embodiment an additional advantage of the sensing signal is that is possible to sense if a crystal has been connected altogether. Thereby it might be prevented destroying the RF driver, which would happen if RF power is applied when there is no crystal connected.

In several applications, the limited bandwidth of a single AOTF makes it attractable to include several complementary AOTFs in a single system (see e.g. FIG. 1). In one embodiment it is not necessary to operate more than one crystal at a time for example if visible and infrared output is not required simultaneously. By switching the RF signal to the crystal of the desired AOTF it is possible to make an implementation with a single RF driver for several crystals and thereby reduce costs. In a simple implementation this can be done by manually routing the RF signal to the desired crystal. There is a risk of error using this approach and it is not very user friendly. Nor does this approach lend itself to highly automated setups. The introduction of an electronically controlled RF switch circumvents this problem, by allowing the signal routing to be done electronically.

The RF switch could e.g. be:
MASW-007587 from Macon Technology Solutions
HSWA2-30DR+ from Mini Circuits
L1 SERIES, DPDT (TRANSFER), DC-26.5 GHz from Charter Engineering, Inc.

In cases where two or more crystals are to be controlled simultaneously it is possible to do this with two or more RF drivers. Alternatively, it can be done using a single driver where the signal is split and routed to the individual crystals (using an RF power splitter). The advantage of this approach is system simplification and cost reduction. Splitting could be for example be applied in configurations such as those of FIGS. 9 and 10.

In one implementation the RF drive frequency to wavelength relationship for the two (or more) crystals can be matched by tuning the relationship for the individual crystals by changing the angle of incidence.

In one implementation the RF drive frequency to wavelength relationships of the two crystals can be matched by controlling the temperatures of the crystal.

The RF power splitter could e.g. be a BNC Female Power Divider; 2-500 MHz from Pasternak Enterprises

BRIEF DESCRIPTION OF DRAWINGS

The invention will be explained more fully below in connection with a preferred embodiment and with reference to the drawings in which.

The figures are schematic and may be simplified for clarity. Throughout, the same reference numerals are used for identical or corresponding parts.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. Furthermore, it should be noted that the scope of the invention also combining a feature from one embodiment with a feature of another embodiment unless the two features are clearly mutually exclusive.

Figure 1A:
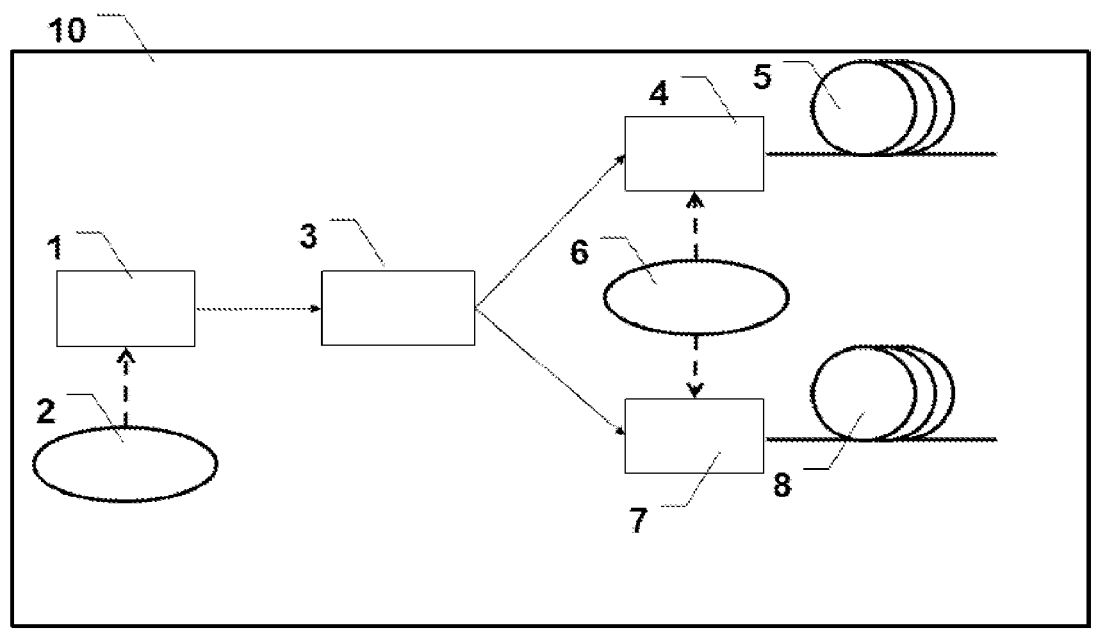
FIG. 1a shows a prior art device for modifying a broadband beam.

FIG. 1a shows a prior art light source with two tunable output wavelengths 10 in prior art. It consists of a broad band light source 1 with an electronic control 2. The output of the broadband source is send into a spectral splitter 3, and subsequently the two outputs is send into two tunable filters 4, 7. The tunable filters are electronically controlled 6 to vary the wavelength and/or the output power. Each tunable filter might emit several wavelengths simultaneously. Furthermore the transmission of the filter might be set independently at each wavelength. The two outputs from the tunable filters are optionally coupled into fiber delivery systems 5, 8, said fiber delivery system might comprise collimating optics.

Figure 1B:
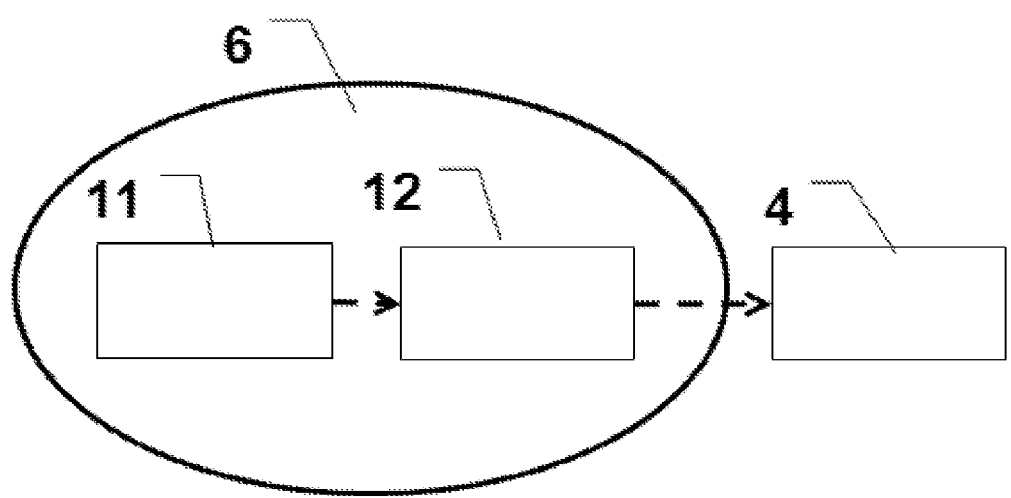
FIG. 1b shows a prior art schematic of the electronic control which is used for the tunable filter.

FIG. 1b shows a prior art schematic of the electronic control 6, which is used for the tunable filter 4. A PC 11 sends a signal into a Direct Digital Synthesis (DDS) RF driver 12, which translates this to an RF modulated driving current that is fed into the tunable filter 4.

Figure 2:
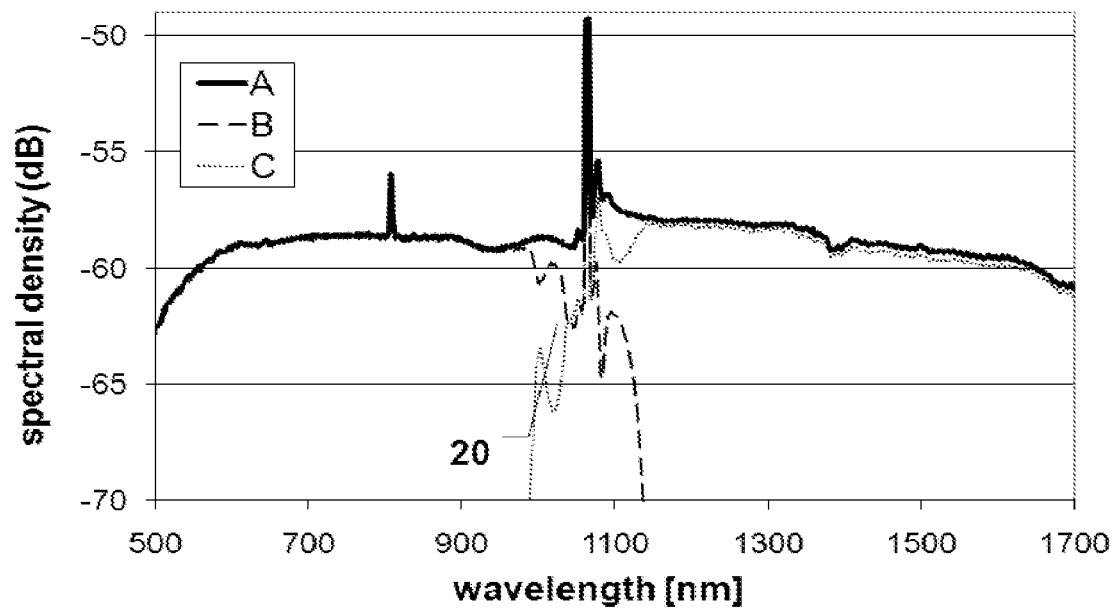
FIG. 2 shows measurements of the optical spectrum of directly after a broad band light source and at the two output arms from a spectral splitter in prior art.

FIG. 2 shows measurements of the optical spectrum in prior art, where A) is directly after abroad band light source 1 and B) and C) at the two output arms from a spectral splitter 3. The figure is taken from patent application WO 2009/095023 A2. In this example the splitting is performed in a dichroic mirror where the low wavelength part is reflected to spectrum B) and the high wavelength part is transmitted to spectrum C). It is observed that an intermediate wavelength range exists 2 where the light is divided into both output spectra.

Figure 3:
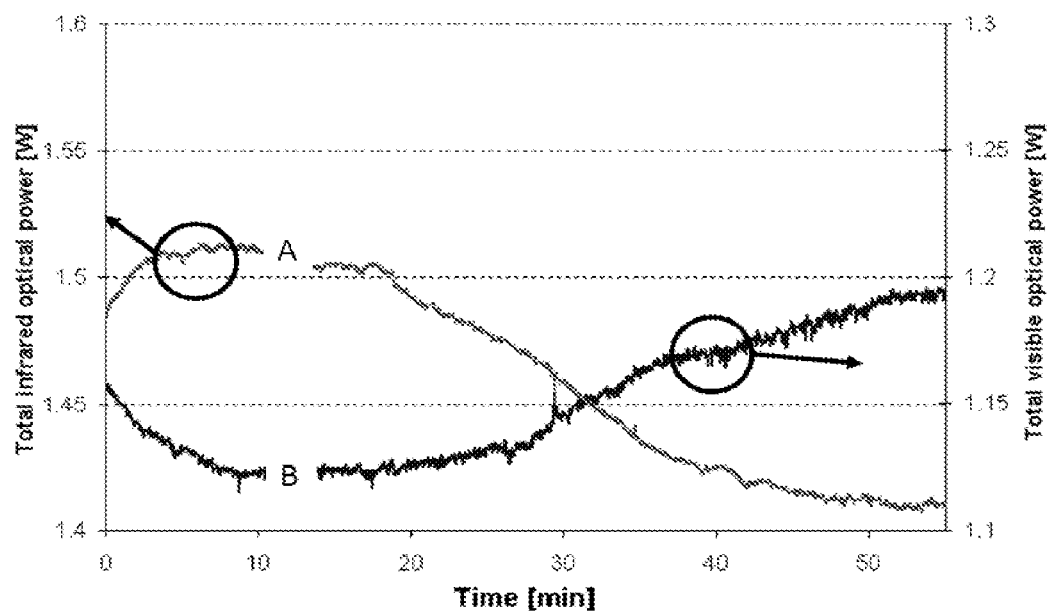
FIG. 3 shows measurements of the optical power at the two output arms from a spectral splitter as a function of time in prior art.

FIG. 3 shows measurements of the optical power at the two output arms from a spectral splitter 3 as a function of time (prior art). Here A) is the power in the output with the infrared light and B) is the power the output with the visible light.

Figure 4:
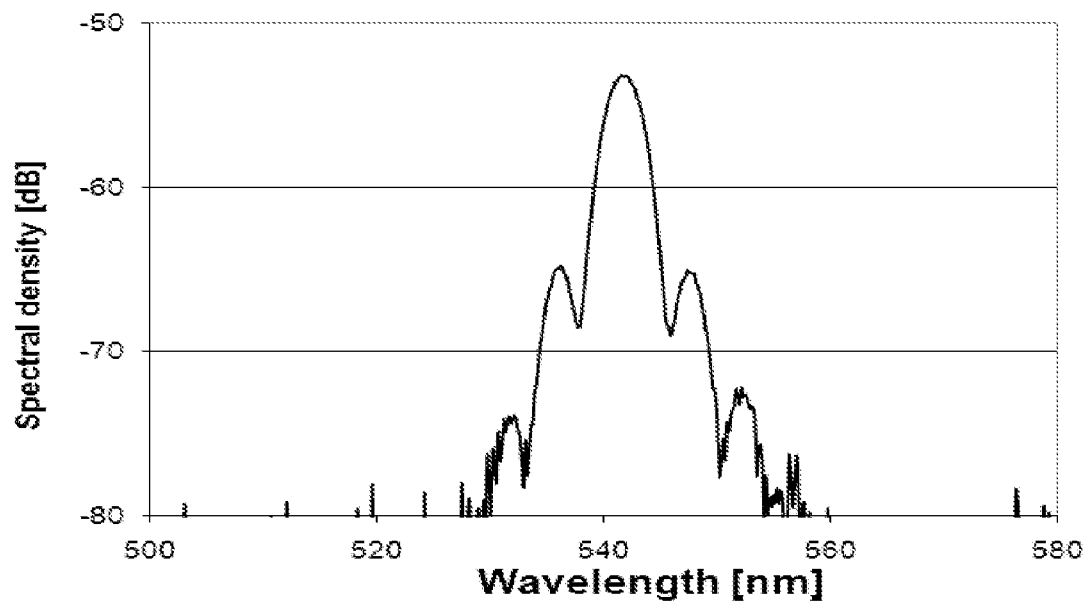
FIG. 4 shows measurements of the optical spectrum after a tunable filter in prior art.

FIG. 4 shows measurements of the optical power after a tunable filter 4. In this example it is set for only emitting one output wavelength (prior art). In one embodiment the tunable filter is an AOTF, which is driven by an RF driver. Here it is possible to emit several wavelengths simultaneously. However, the wavelengths should be separated by at least 3 dB bandwidth of the output in order to avoid Beating in the RF signal.

Figure 5A:
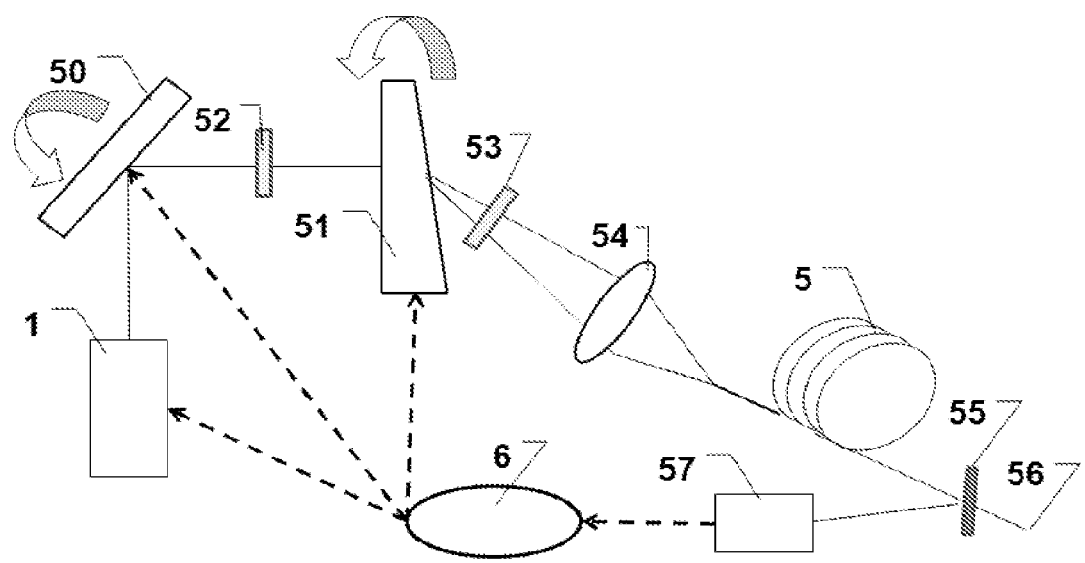
FIG. 5a shows a tunable broad band filter according to one embodiment of the invention.

FIG. 5a shows a tunable broad band filter according to one embodiment of the invention. The output of the broad band source 1 is directed to mirror 50 and a dispersive element 51. Either the mirror and/or the angular dispersive element are connected to an electronic control 6, which enables a rotation between these two elements. The system might optionally also include a tunable damping filter 52 and/or a tunable spatial filter 53. The light is collimated by a lens system 54 and collected by a fiber 5, which thereby also works as a spatial filter. The system might optionally include a broadband splitter 55, which sends the majority of the light to the output 56 and a small part of the light to a detector system 57. Said detector system is connected to the electronic control system 6, which again is connected to the broad band source 1 and /or the mirror 50 in order to stabilize the output power. In one embodiment the fiber is a single mode fiber or and endlessly single mode fiber. In one embodiment the collimating lens system 54 and the fiber 5 are combined in a fiber delivery system. In one embodiment the collimation lens system 54 comprises multiple lenses. In one embodiment the mirror 50 is a dichroic mirror, which separates out the undesired wavelength range in order to limit thermal load on the system. In one embodiment there is at least one additional mirror before the angular dispersive element 51. In one embodiment one of the mirrors might be rotated in two perpendicular directions to provide both control of the central wavelength and the output power. The angular dispersive element 51 might comprise a wedge, prism or other optical elements that disperse the light. In one embodiment the filtering system is used for OCT.

Figure 5B:
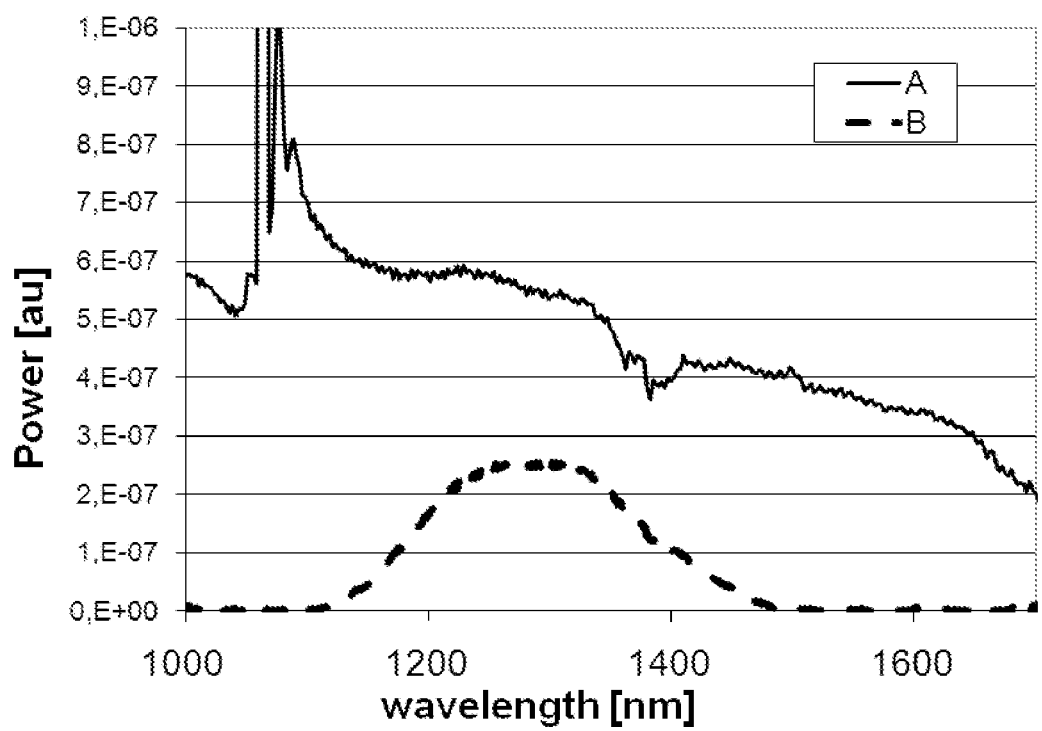
FIG. 5b shows the measured spectrum from a broad band source and after a tunable filter according to the invention.

FIG. 5b shows the spectrum from a broad band source (A) and after a tunable broad band filter according to the invention (B). It is observed that the output from the filter has a Gaussian like shape, even though the spectrum from the broad band source is not flat in the utilized wavelength range.

Figure 5C:
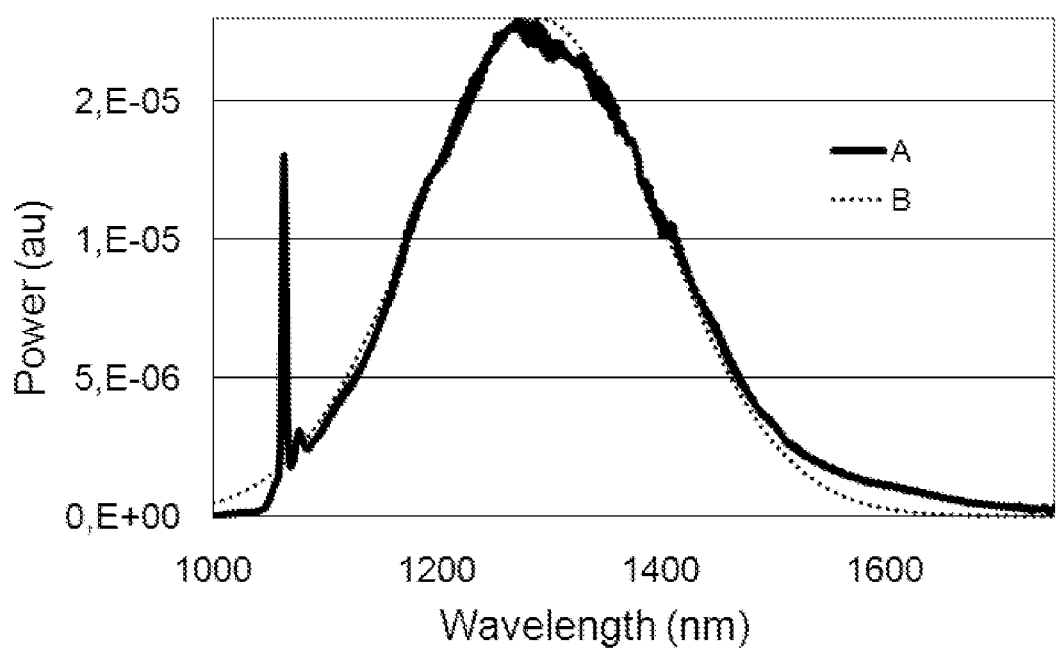
FIG. 5c shows the measured spectrum from a broad band source and after a tunable filter according to the invention. In this case the filtered spectrum contains a spike.

FIG. 5c shows the spectrum after a tunable broad band filter according to the invention (A) and a Gaussian fit to this spectrum (B). The spectrum comprises a spike of light at 1060 nm, which stems from the broad band source. In one embodiment this spike is removed by utilizing a spatial filter 53 after the angular dispersive element.

Figure 6:
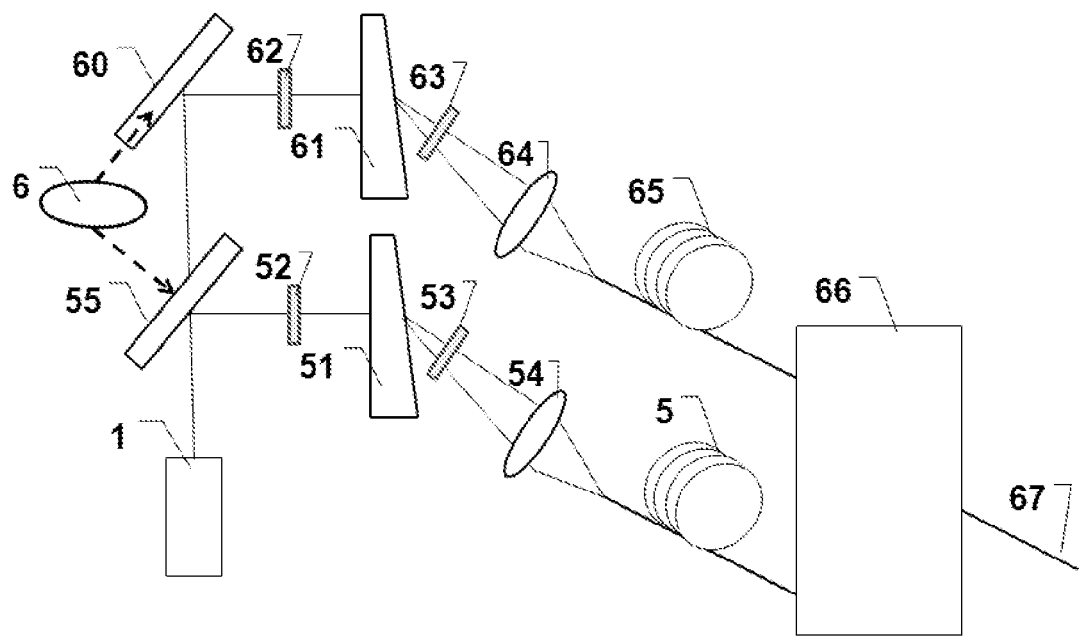
FIG. 6 shows a method of obtaining two tunable broad band spectral outputs according to one embodiment of the invention.

FIG. 6 shows a method of obtaining two tunable broad band spectral outputs according to one embodiment of the invention. The output of the broad band source 1 is directed to a dichroic mirror, which separates the low wavelength and high wavelength part of the spectrum. Each of these outputs is filtered as described in FIG. 5. The two output spectra are independently tunable through the electronic control 6, which enables a rotation between the two mirrors and angular dispersive elements. Finally the two outputs are combined in 66 to a single output 67. The combiner 66 might comprise a wavelength multiplexer, such as a fiber WDM or a dichroic mirror or other wavelength dependent filters. In one embodiment the system is used for dual band OCT.

Figure 7:
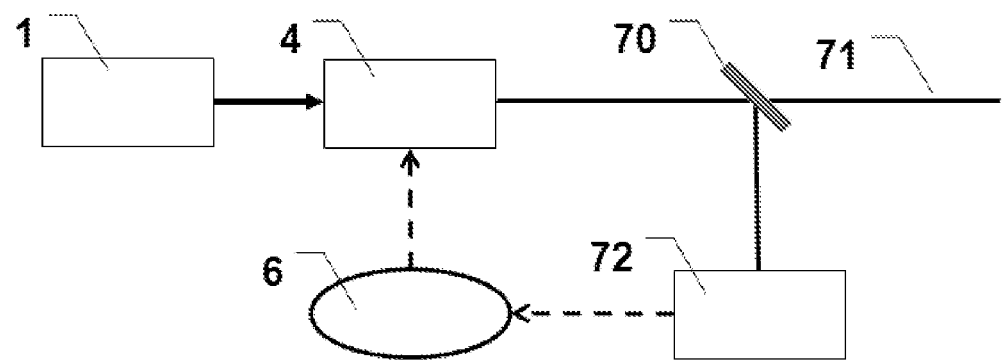
FIG. 7 shows a method for simultaneous stabilizing the output at multiple wavelengths according to one embodiment of the invention.

FIG. 7 shows a method for simultaneous stabilizing the output at multiple wavelengths according to one embodiment of the invention. The output of the broad band source 1 is directed to a tunable filter 4, which transmits one or more wavelengths from the spectrum. These wavelengths are sent to a broadband splitter 70. The splitter sends the majority of the light to the output 71. However a small portion of the light is directed to a wavelength dependent detector 72, which is connected to the control of the tunable filter 6. In this example the controller is programmed so that a feedback loop is formed and ensures that the transmission of the filter at each wavelength is varied to maintain the measured power at this wavelength constant. In one embodiment the wavelength dependent detector is a spectrometer, such as e.g. Ocean Optics USB2000+. In the present context wavelength dependent detector is intended to mean that the detector provides substantially separate measurements for a set of wavelengths or wavelength ranges, such as a spectrometer. In one embodiment stabilization is further or alternatively provided by an LCD or DLP filter applied as a tunable dampening and/or tunable spatial filter for example as part of a feedback loop.

In one embodiment feedback is based on a single or a few optical wavelengths. In one such embodiment the splitter 70 is not necessarily broadband and/or the detector 72 is not wavelength dependent.

In one embodiment the wavelength dependent detector 72 is placed upstream of the tunable filter 4 thus included the transfer function of the tunable filter in the signal detected by the detector 72. In one such embodiment a feed forward signal is transmitted to the tunable filter 4 based on the output of the detector 72 so as to stabilize the output from the filter 4.

It is clear from the previous description that the tunable filter 72 may be any of the tunable filters discussed in this text.

In one embodiment it is preferable that the function of the broadband splitter 70 is obtained from an optical component also having another optical function. In one embodiment such a component is a lens or another transmissive component, where the small portion directed to the detector is a residual reflection from the surface of the component. In one embodiment said residual reflection originates from a transition from an unguided section to said transmissive optical component, and in one embodiment said residual reflection originates from a transition from said transmissive optical component to said unguided section. By way of the invention a feedback loop may be implemented without introducing additional optical components which could otherwise introduce optical loss and/or optical aberrations. This approach of using an optical component having another function may be implemented in any of the feedback or feed forward loops of the present text for example as the broadband splitter of 55. Using residual light for feedback in a broadband light source is further described in pending U.S. patent application 2010/0329292 incorporated herein by reference.

In one embodiment the small portion of light is directed to the detector is guided by an optical fiber such as a multimode optical fiber.

In one embodiment it is preferable to collect the feedback signal in the optical system utilizing the light from the broadband light source system, such as a microscope. In this way changes in spectral distribution and/or power level in the applied light may be compensated in the light source. In this context a broadband light source system is a light source 1, optionally combined with a tunable filter, providing an output beam for utilization in another optical system. In one embodiment on or more of the configurations shown in FIGS. 1, 5a, 6-10, 13-15, 17-19 constitutes a broadband light source system. In one embodiment the broadband splitter 70 or the component providing residual light is placed after the broadband light source. In one embodiment the detector 72 is similarly placed in the system utilizing the light from the broadband source and an electrical signal is fed back to the light source system. However, in one embodiment the detector is placed with the broadband light source and the small portion of light is returned to the light source system, e.g. via a dual-y cable. In one embodiment, this method of providing a feedback loop by collecting a small portion of the light at or in the system utilizing the output from the light source system is applicable in any of the feedback loops discussed in the present text.

Figure 8:
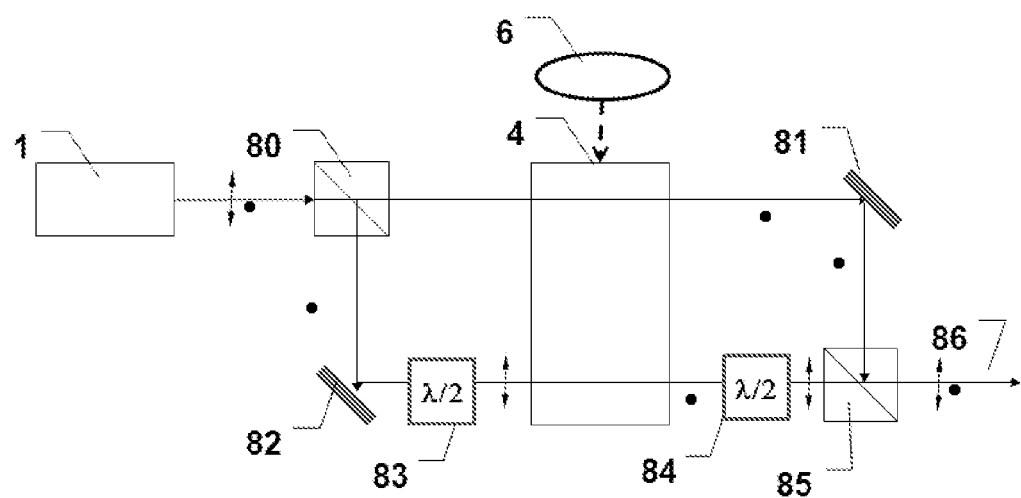
FIG. 8 shows a method of increasing the output power after the tunable filter.

FIG. 8 shows a method of increasing the output power after the tunable filter. Typically the tunable filters only work for light in one polarization, e.g. if the filter is an AOTF. Thus all light in the unwanted polarization is dumped. To circumvent this problem the light from the broad band source 1 is sent into a polarization beam splitter (PBS) 80. The first polarization is transmitted by the PBS 80 and sent to the tunable filter 4, reflected by a mirror 81 and reflected by a second PBS 85 and to the output 86. The second polarization is reflected by the PBS 80 onto a mirror 82 and thereafter through a half wave plate 83, which changes the polarization by 90 degrees so it is identical to the polarization of the first beam. Subsequently it is sent through the same tunable filter 4 as the first polarization, another half wave plate 84 and transmitted through a second PBS 85. Finally it is combined with the first polarization in the second PBS 81. In practice this might require making tunable filter with larger working area than conventional solutions. In one embodiment the working area of the tunable filter is 10 mm. In one embodiment the PBS comprises a Glan prism. In one embodiment the PBS 80, mirror 82 and half wave plate 83 are integrated into a single component. By using the same filter for both polarizations substantially the same filter function is applied so that substantially all wavelengths are doubled relative to only using a single polarization.

Figure 9:
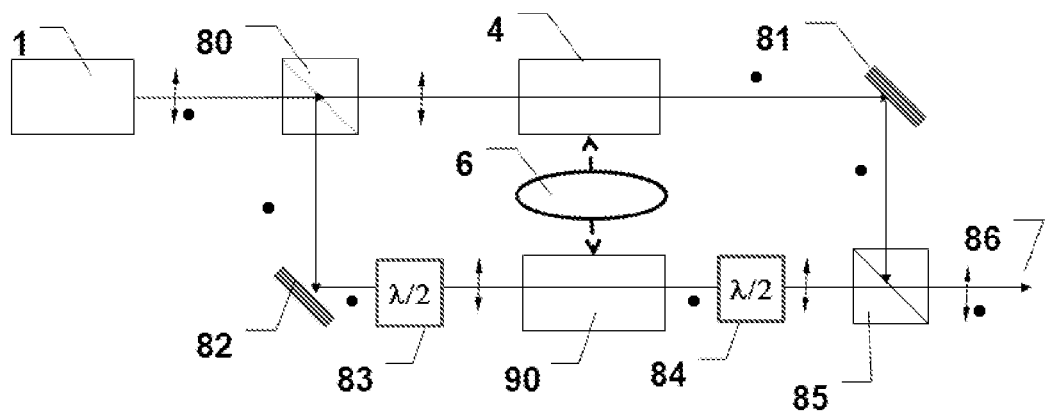
FIG. 9 shows a method of enabling fast polarization switching and increasing the output power after the tunable filters.

FIG. 9 shows a method of enabling fast polarization switching and increasing the output power after the tunable filter. The set-up is similar to FIG. 8, except for that now the second polarization is sent through a second tunable filter 90. Both tunable filters are controlled by the electronic control system 6. However the control system is configured in such a way that the control signal to the two tunable filters is independent. In one embodiment the two tunable filters have substantially the same wavelength response, e.g. the filters are calibrated to perform in a similarly and/or are off the same type. Another advantage of this configuration is that it enables increasing the bandwidth after the filters, by interleaving the outputs from the two tunable filters. By adjusting the control signal to one and/or both filters the magnitude of the output of each filter is in one embodiment adjustable. In one such embodiment one or both filters are AOTFs where the output efficiency may be adjusted via the amplitude of the control signals to said filter. By adjusting the magnitude of the output from the filters the output polarization may be manipulated. In one embodiment polarization switching is provided by turning the filters on and off respectively. In one such embodiment the out 86 is applied in a birefringence measurement of a sample thus allowing the sample to be probed with a beam having controllable polarization properties.

Figure 10:
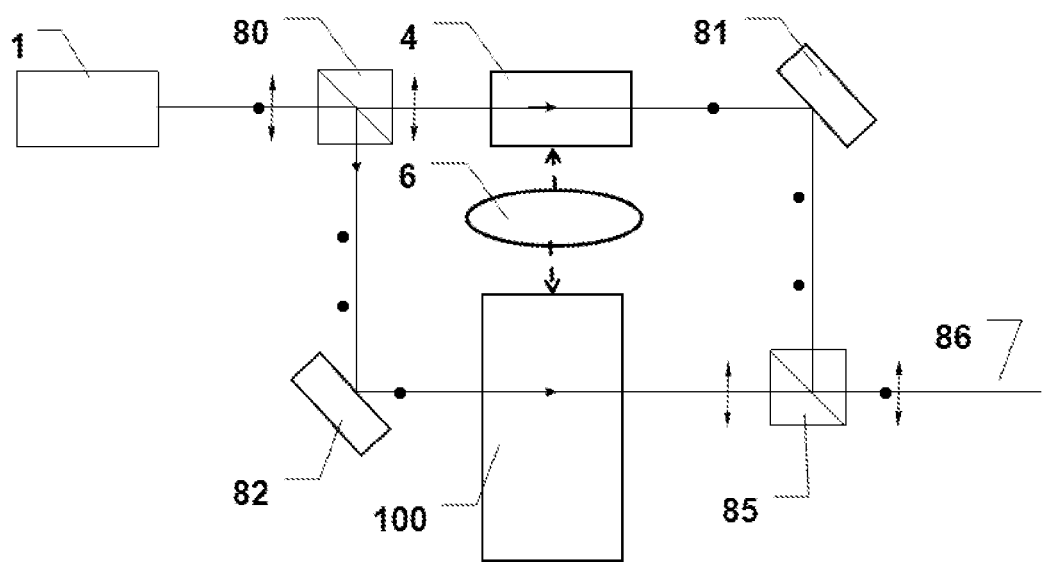
FIG. 10 shows another method of enabling fast polarization switching and increasing the output power after the tunable filters.

FIG. 10 shows another method of enabling fast polarization switching and increasing the output power after the tunable filter. The set-up is similar to FIG. 9, except that the two half wave plates are removed and instead the second tunable filter is rotated by 90 degrees 100.

Figure 11A:
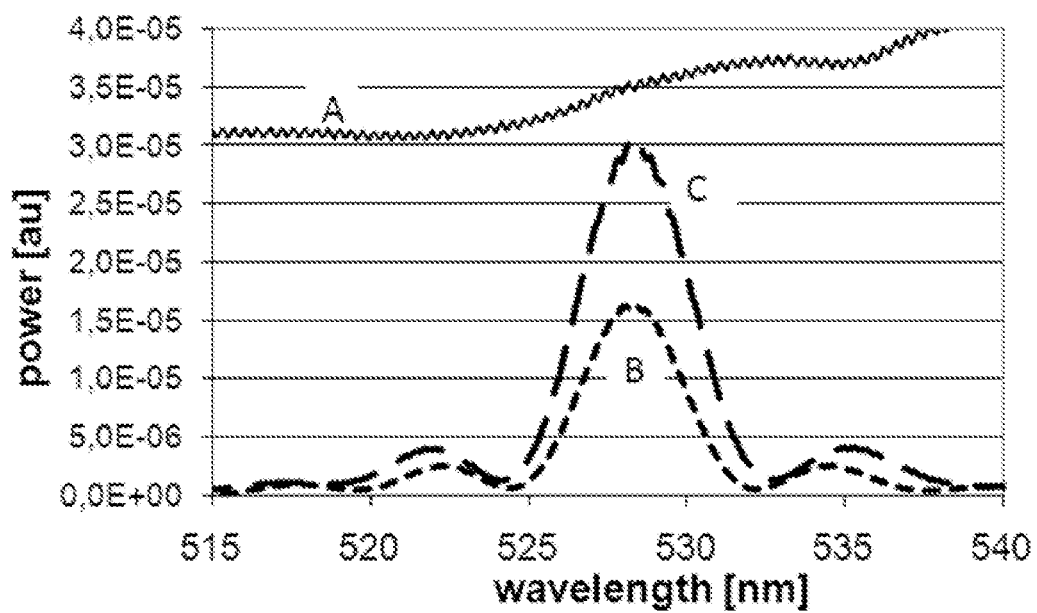
FIG. 11a shows measured spectra for the broadband source and filters shown in FIG. 10.

FIG. 11a shows the results of an experiment with a light source and filter according to FIG. 10. Curve A) is a spectrum for the broadband source 1), B) is the spectrum after one of the tunable filters 4 and C) is the spectrum after the output from the two tunable filters have been combined 86).

Figure 11B:
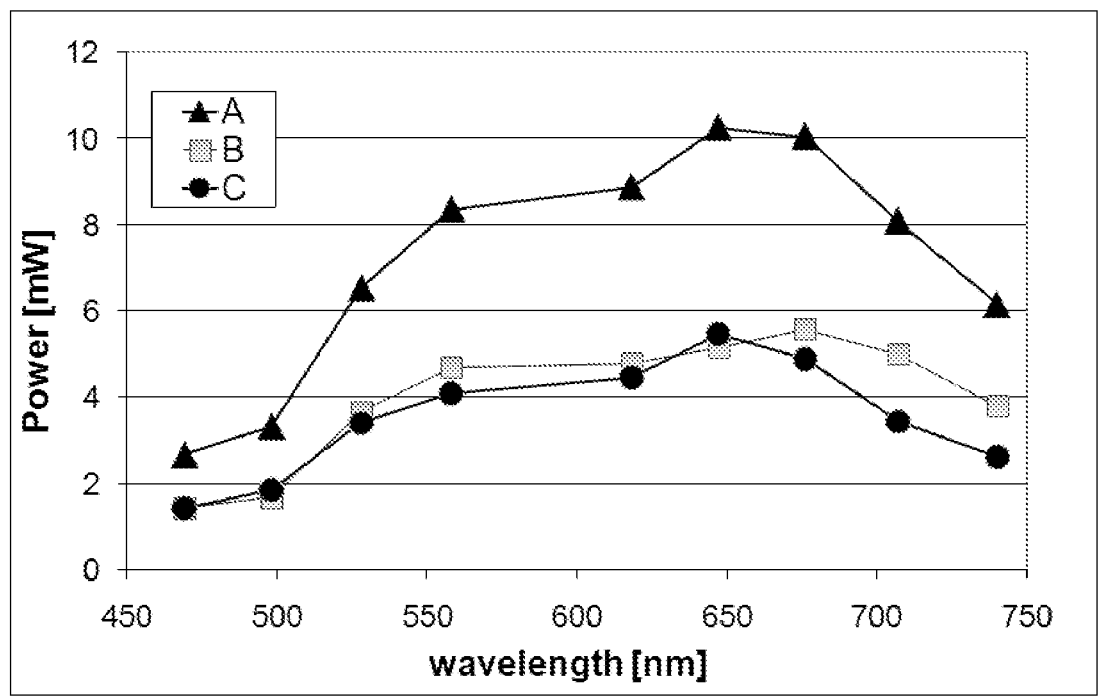
FIG. 11b shows the measured power after the two tunable filters shown in FIG. 10 as well as the output obtained by combining these two.

FIG. 11b shows A) and B) output after the output from the two tunable filters 4, 100 as well as the output obtained by combining these two C). Each point in the curve represents a measurement similar to the one shown in FIG. 11.

Figure 12:
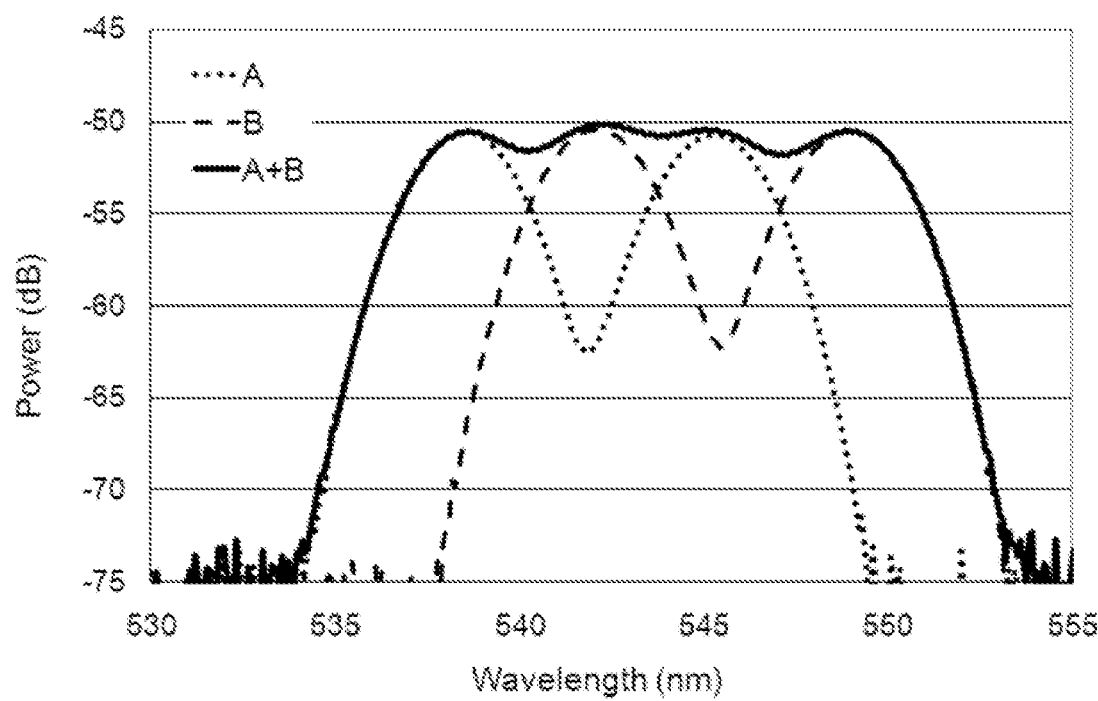
FIG. 12 shows measured output spectra after the two tunable filters from FIG. 10 and as well as the combined output.

FIG. 12 shows A) and B) output after the two tunable filters 4, 100, as well as A+B) the combined output. In this example the outputs from the two tunable filters are spectrally displaced, so the combined output is broader than the output from the individual filters. The light in A and B have different polarizations.

Figure 13:
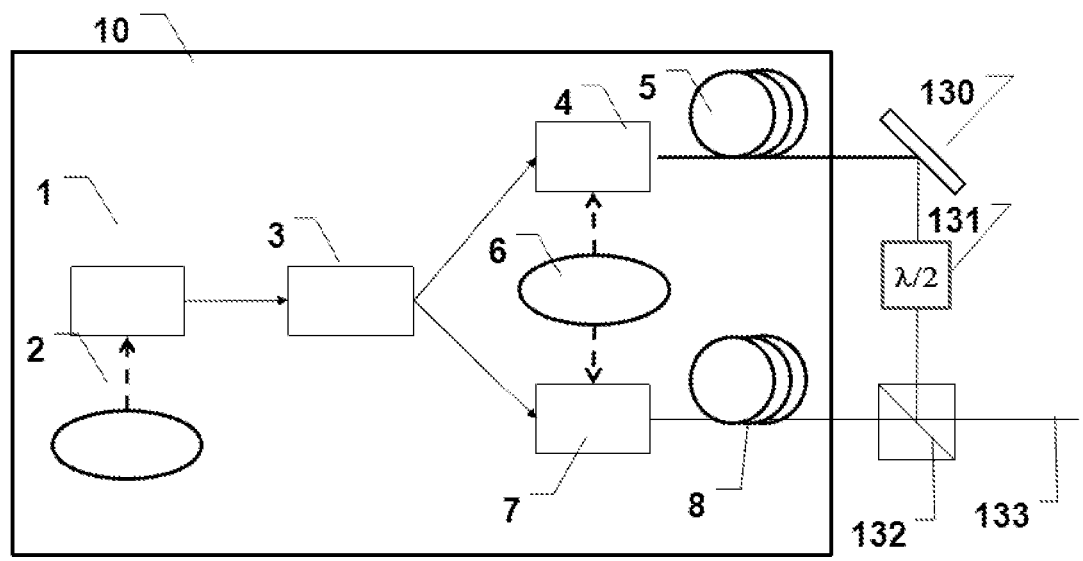
FIG. 13 shows a method for combining the outputs of a light source with two tunable outputs.

FIG. 13 shows a method for combining the outputs of a light source with two tunable outputs 10. The output from the first tunable filter 4 is reflected by a mirror 130 and sent through a half wave plate 131. Subsequently it is combined with the output from the second tunable filter 7 in a polarization beam splitter 132. As the two filter 4, 7 have different spectral bandwidths the combined output 133 is now tunable over a very wide range. In addition it is possible having both tunable filters operating at the intermediate wavelength region 20, where the light is divided to both output arms. By combining the two outputs it is thus possible to increase the power in this wavelength region. In an alternative embodiment the combining beam splitter 132 is replaced by a spectral splitter, e.g. a dichroic mirror arranged to combine the beams from the filter 4, 7 hence utilizing the different spectral range of the outputs from the filter to perform the combination.

In one of the preceding embodiment the two filters 4, 7, 90, 100 are AOTFs provided with control signals controlled by a VCO. By combining the beams using either a polarization splitter or a spectral splitter the number of lines in a single beam may be increased.

Figure 14:
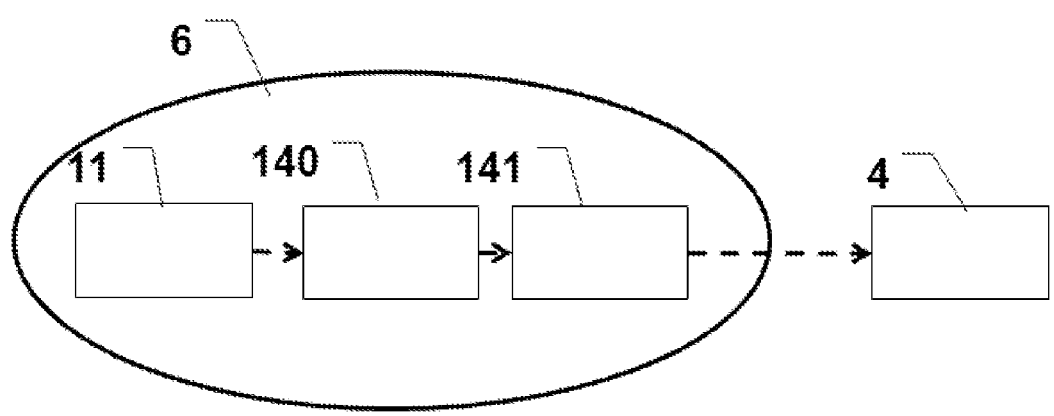
FIG. 14 shows a schematic of the electronic control, which is used for the tunable filter in one embodiment of the invention.

FIG. 14 shows a schematic of the electronic control 6, which is used for the tunable filter 4. A PC 11 sends a signal to a DA board 140 and subsequently into a Voltage controlled oscillator (VCO) RF driver 141, which translates this to an RF modulated driving current that is fed into the tunable filter 4 optionally via an amplifier arranged to boost the RF signal. In one embodiment the frequency is swept. In one embodiment the sweep is utilized for fast synthesizing of a broad band output for hyper spectral measurement. In one embodiment the sweep is used for synthesizing an arbitrary spectrum. In one embodiment said arbitrary spectrum is a Gaussian.

Figure 15:
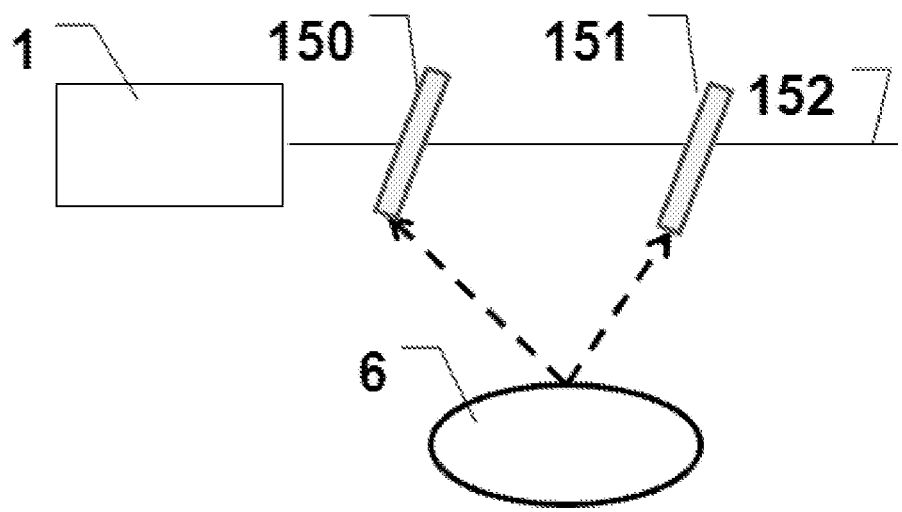
FIG. 15 shows a method for filtering the output using variable filters, in which the transmission spectra change with position over the filter.
Figure 16:
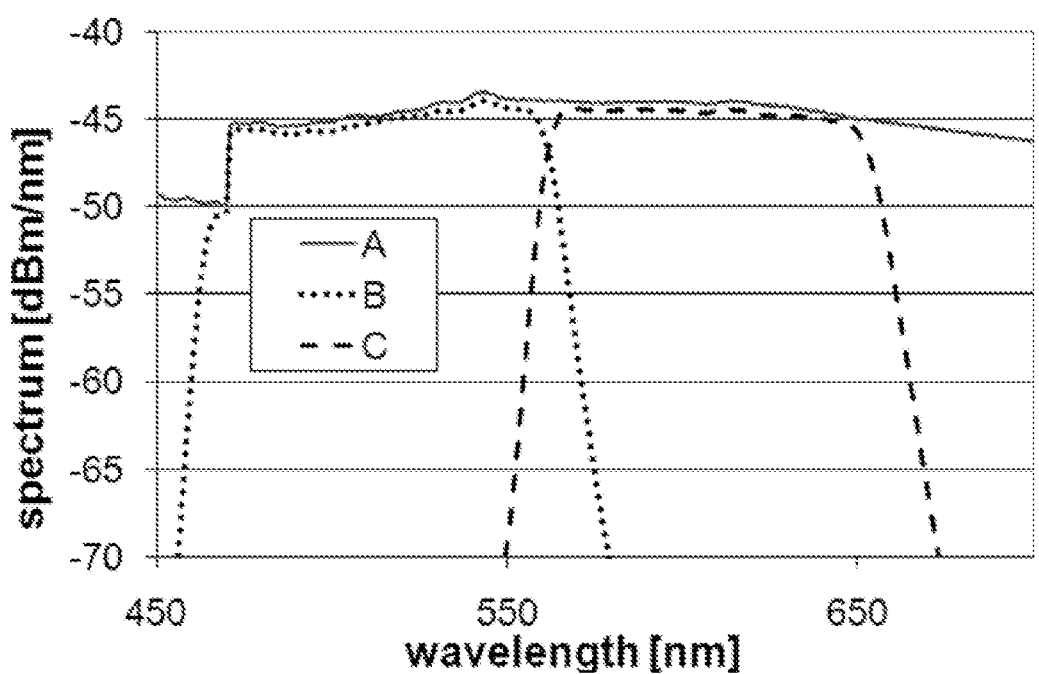
FIG. 16 shows the measured spectra obtained by filtering a broadband source with two variable filters.

FIG. 15 shows a method for filtering the output using variable filters, in which the transmission spectra change with position over the filter. The output from the broadband source 1 is filtered by a variable long wave pass filter 150 (i.e. high-pass filter) and a variable short wave pass filter 151 (i.e. a low-pass filter to the output. Both the variable filters are connected to an electronic control 6, which enables moving the filters to change their transmission spectra. In one embodiment the beam is first transmitted by the variable long wave pass and subsequently the variable short wave pass filter. In one embodiment said variable filters are linear variable filters. Linear variable filters can e.g. be acquired from the Danish company Delta Light and Optics, Ho/rsholm, Denmark. In one embodiment either the variable long wave pass or the variable short wave pass filter is omitted. In one embodiment said linear variable filters have an out of band suppression of more than or equal to 10 dB, such as more than or equal to 15 dB, such as more than or equal to 20 dB, such as more than or equal to 30 dB, such as more than or equal to 40 dB, such as more than or equal to 50 dB, such as more than or equal to 60 dB. In one embodiment an advantage of such linear variable filter is a high out-of-band suppression. For some applications, e.g. fluorescent measurements/microscopy, a high out-of-band suppression is preferred or even required in order to allow detection of the fluorescent signal. In one embodiment the out-of-band suppression is defined as discussed in respect to the application of VCO above. FIG. 16 the spectra obtained by filtering a broadband source with two variable filters. Here A) is the spectrum from the broad band source, B) is the spectrum optimized by one setting of the filters and C) is the spectrum obtained by another setting of the filters.

Figure 17:
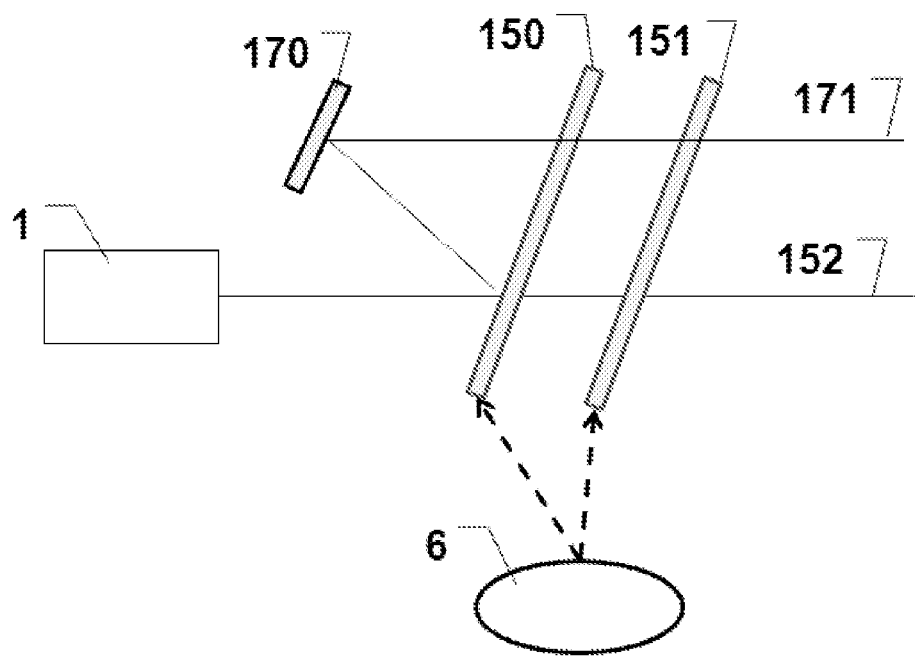
FIG. 17 shows a method of obtaining two tunable spectral outputs using variable filters.

FIG. 17 shows a method of obtaining two tunable spectral outputs using variable filters. As in FIG. 15, the output from the broadband source 1 is filtered by a variable long wave pass filter 150 and a variable short wave pass filter 151 to the output 152. In addition the reflected beam from the variable long wave pass filter is utilized. Said second beam is reflected by a mirror 170 and sent through the variable filters 150 and 151. However, said second beam will traverse different positions than the first beam, which will lead to different filter properties. Thus the second output 172 will contain different wavelengths than the first output 152. In one embodiment the reflection of said second beam on the long wave pass filter 150 is utilized to form a third beam, which is also filtered by said variable filters 150, 151.

Figure 18:
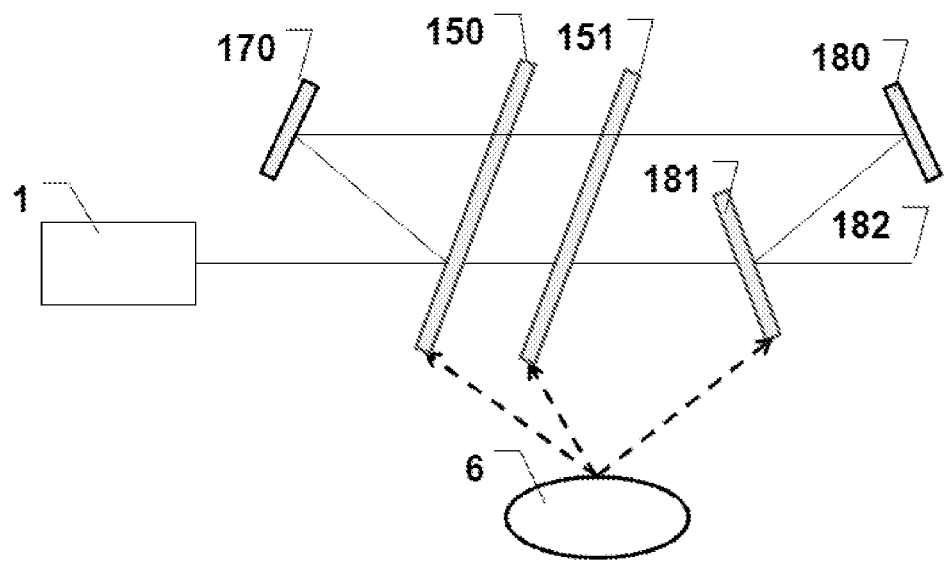
FIG. 18 shows a method of combining the two tunable spectral outputs from FIG. 17.

FIG. 18 shows a method of combining the two tunable spectral outputs from FIG. 17. As in FIG. 17, two beams are passing through the variable filters 150, 151 at different position. Furthermore the second beam is reflected by a second mirror 180 and multiplexed with the first beam in a second variable short wave pass filter 181, where the transmission spectra of said second short pass filter is electrically controlled to match the transmission spectra of the first short pass filter 150.

Figure 19:
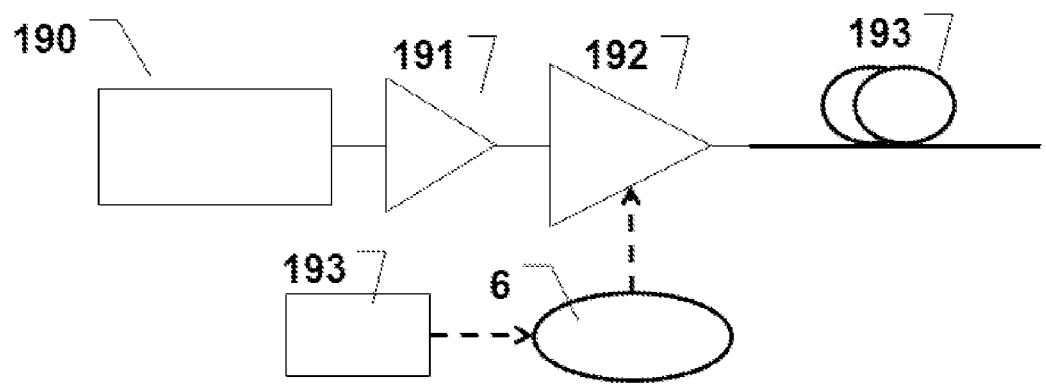
FIG. 19 shows a method of extending the lifetime of a super continuum source.
Figure 20:
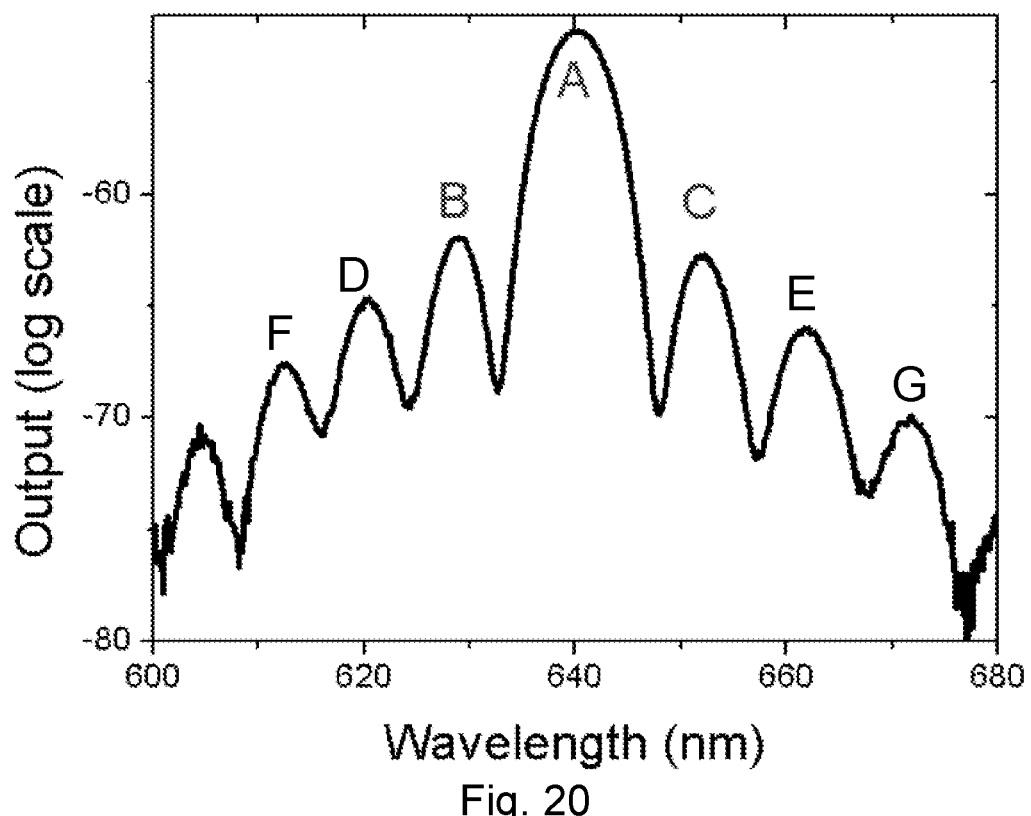
FIG. 20 shows an exemplary filter function of an AOTF.

FIG. 19 shows a method of extending the lifetime of a super continuum source. It consists of a SEED laser 190, an amplifier chain 191, 192 and a nonlinear fiber 193. The last amplifier in the chain is controlled by an electronic control 6, which is connected to an external control 193. The external control allows fast switching between high and low current to last amplifier and thereby the input power to the nonlinear fiber. In one embodiment the external control is integrated with the super continuum light source. In one embodiment the external control sends out a trigger signal to the last amplifier, such that the current changes from high to low, or from low to high. The trigger signal may in principle be any suitable signal arranged to control the amplification of the second amplifier. In one embodiment a variable attenuator or switchable beam block is arranged between the output of the amplifier 192 and the fiber 193 to control the power delivered to the fiber. For some applications high output power is not needed all the time, but fast turn on time is important. In such an embodiment the supercontinuum light source or the system incorporation the light source, such as a microscope or another application of a broadband source discussed text, can be said to have an operation mode last amplifier 192 of the supercontinuum light source provide a high amplification. For these applications the external control option allows the user to obtain light when required, which increases the number of usage hours of the system. In one embodiment the lifetime of the system is limited by the lifetime of the nonlinear fiber and the lifetime of the nonlinear fiber is decreasing with the input power to said fiber. In one embodiment said rate of decrease is initially relatively low, but it increasing with the input power to the nonlinear fiber. In prior art (WO 2009/024490) the external control feature allows the user to switch the last amplifier 192 on and off with a fast rise time. However, switching the last amplifier on from the off state might lead to a significant thermal change in the system, which temporarily decreases the stability, such providing fluctuations on the output from the fiber in the order of 10 to 20% after 100 ms of turning on the last amplifier 192. In one embodiment the life of the fiber increases significantly by reducing the pump light to the fiber with e.g. 20% or even less. In one embodiment according to the invention, the external control does not switch the last amplifier completely off, but causes the amplifier to reduce its amplification. In this case the supercontinuum light source or the system incorporation the light source can be said to have a low power mode where the last amplifier of the supercontinuum light source provide an amplification which is lower relative to the amplification in the operation mode. In one embodiment said low current is such as around 75% of the high current, such as around 50% of the high current, such as around 25% of the high current, such as around 10% of the high current. In one embodiment the external control causes the last amplifier to reduce the amplification of the last amplifier. In one embodiment said amplification is less than or equal to 95% of the amplification during operation, such as less than or equal to 90%, such as less than or equal to 85%, such as less than or equal to 80%, such as less than or equal to 75%, such as less than or equal to 70%, such as less than or equal to 60%, such as less than or equal to 50%, such as less than or equal to 40%, such as less than or equal to 30%, such as less than or equal to 20%, such as less than or equal to 10%. Accordingly, in one embodiment the invention relates to a supercontinuum light source as described above and the use of that light source in a system, wherein the supercontinuum lights source has at least the mentioned operation and low power modes. In one embodiment application of the low power mode provides for stable output within less than 5% after 100 ms of switching to operation mode. In one embodiment the output is stable with less than 4%, such as less than 3%, such as less than 2%, such as less than 1.5%, such as less than 1%, such as less than 0.5%. In one embodiment these stability measurement are measured within a wavelength range such as 400 to 450 nm such as 600 to 700 nm or such as 400 to 700 nm. In one embodiment these stability measurements are added instability relative to residual instability of the light source present after relative long operation time in operation mode. Long time is in one embodiment longer than 1 minute, such as longer than 2 minutes, such as longer 5 minutes, such as longer than 10 minutes, such as longer than 30 minutes, such as longer 1 hour.

The invention is defined by the features of the independent claim(s). Preferred embodiments are defined in the dependent claims. Any reference numerals in the claims are intended to be non-limiting for their scope.

Some preferred embodiments have been shown in the foregoing, but it should be stressed that the invention is not limited to these, but may be embodied in other ways within the subject-matter defined in the claims.

EXAMPLE 1

A system for making a broad tunable spectral was constructed a shown in FIG. 5. The broad band source is a SuperK Compact from NKT Photonics.

In addition the following components were used:

| Item | Specification | part No. | Vendor |
|---|---|---|---|
| Angular dispersive element 1 | 4° Round Wedge Prism, Ø25.4 mm, AR Coating: 650-1050 nm | PS-811B | Thorlabs |
| Angular dispersive element 2 | 10° Round Wedge Prism, Ø25.4 mm, AR Coating: 1050-1580 nm | PS-814C | Thorlabs |
| fiber 1 | single mode fiber, 630-860 nm, cut off 590 +/− 30 nm | S630-HP | Thorlabs |
| fiber 2 | single mode fiber 980/1064/1550 nm, cutoff 920 +/− 50 nm | SM980-5.8-125 | Thorlabs |
| Lens 1 | achromatic lens, Ø3, F5, ARB1 VIS | G612-066-000 | Linos |
| Lens 2 | achromatic lens, Ø3, F5, ARB1 IR | G612-067-000 | Linos |

In order to obtain wavelength tuning the mirror before the angular dispersive element was turned. The typical angles were typically less than 1 degree. The resulting change in central wavelength can be calculated by using Snells law.

EXAMPLE 2

A method of enabling fast polarization switching and increasing the output power after the tunable filters was constructed as shown in FIG. 10. The broad band source is a SuperK Compact from NKT Photonics.

In addition the following components were used:

| Item | Specification | Part No. | Vendor |
|---|---|---|---|
| Spectral Splitter | Ø25.4 × 6 mm, HR400-800/HT900-2400 | WNH0204 | Casix |
| AOTF1 and 2 | VIS 400-800 nm, 8 channels | 97-02885-04 | CTI |
| Polarization Beam Splitters | 400-900 nm, PER > 23 dB for both directions | PGL01 | Dayoptics |
| Mirror | Ø25.4 × 6 mm, HR 400-80 nm | E02 | Thorlabs |

Embodiments of the invention are further specified according to the following set of items:
1. A filter for filtering an incoming broadband beam, the broadband beam defining a beam path through said filter; said filter comprising
    beam guiding optics arranged to guide an incoming broadband beam along a first portion of said beam path;
    an angular dispersive element arranged so that said first portion of said broadband beam is incident on a first surface of said angular dispersive element at an incident angle, whereby light at different wavelengths of the broadband beam are exiting said angular dispersive element in different angles providing an angular dispersed beam,
    a coupling lens arranged after said angular dispersive element, said lens being arranged to provide focusing at least part of said angular dispersed beam to a spot at a first position along the beam path; and
    an optical waveguide comprising a light guiding portion and an end facet arranged at said first position so that the light guiding portion collects at least part of the beam focused into said spot.
2. The filter according to item 1, wherein the angular dispersed beam in said spot has a larger cross sectional diameter than the cross sectional diameter of the light guiding portion such that only light in one wavelength range of said incoming angular dispersed beam is collected by said light guiding portion and light at wavelengths outside said one wavelength range is filtered out.
3. The filter according to item 1 or 2 wherein said first position is substantially in a focal plane of said coupling lens.
4. The filter according to item 1 or 2 wherein said first position is plane offset from a focal plane of said coupling lens.
5. The filter according to any of items 2 to 4, wherein the one wavelength range has a spectra shape with a spectral width $\Delta\lambda$, and a central wavelength $\lambda_c$.
6. The filter according to any of items 1 to 5, wherein said beam guiding optics comprises at least one reflective element arranged to guide said broadband beam along said first portion of the beam path.
7. The filter according to item 6, wherein said reflective element comprises a mirror.
8. The filter according to item 7, wherein at least one of said mirrors is a d0ichroic mirror.

9. The filter according to any of items 6 to 8, wherein the reflective element and/or the angular dispersive element are arranged to be rotatable relative to the portion of the beam path between these elements.
10. The filter according to any of items 1 to 9, wherein the filter is tunable with respect to the central wavelength.
11. The filter according to any of items 1 to 10, wherein said spot and said end facet can be moved relative to each other in such a manner that said central wavelength is tuned.
12. The filter according to any of item 1 to 11, wherein the incident angle of said first portion of said beam path relative to said angular dispersive element can be changed such that said central wavelength is tuned.
13. The filter according to item 12, wherein said incident angle is changed by rotating said angular dispersive element relative to said first portion of said beam path.
14. The filter according to any of items 1 to 13, wherein the reflective element is rotatable such that the first portion of said beam path is changed and such that said incident angle changes.
15. The filter according to any of items 1 to 14, comprising a control unit arranged to control the relative orientation of the angular dispersive element and the beam guiding optics.
16. The filter according to any of items 1 to 15, wherein the spectral width of the filtered broadband beam is in the range of about 10 nm to about 1000 nm, such as in the range of about 20 nm to about 700 nm, such as in the range of about 30 nm to about 500 nm, such as in the range of about 50 nm to about 400 nm.
17. The filter according to any of items 1 to 16, wherein the central wavelength of the filtered broadband beam is in the range of about 400 nm to about 2000 nm, such as in the range of about 500 nm to about 1500 nm.
18. The filter according to any of items 1 to 17, wherein the distance between the coupling lens and the fiber end facet can be changed such that the cross sectional dimension of the spot at said fiber end facet changes and the spectral width of the filtered broadband beam is tuned.
19. The filter according to any of items 1 to 18, wherein the dimension of said spot along which the wavelength of the light in said spot varies is larger than the cross sectional dimension of the light guiding portion along that dimension.
20. The filter according to any of items 1 to 19, wherein said angular dispersive element is selected from the group of a wedge, or a prism and a diffractive element.
21. The filter according to any of items 1 to 20, wherein said optical waveguide is an optical fiber.
22. The filter according to item 21, wherein said optical fiber is a single-mode optical fiber.
23. The filter according to item 21, wherein said optical fiber is a microstructured endlessly single-mode optical fiber.
24. The filter according to any of items 1 to 23 wherein a spatial filter element is arranged in said beam path, preferably between said angular dispersive element and said coupling lens.
25. The filter according to any of items 1 to 24, wherein said spectral shape is selected from the group of a Gaussian profile, a Lorentzian profile, a Bessel profile, a Voigt profile or a super Gaussian profile.
26. The filter according to any of items 1 to 25, comprising a monitoring unit arranged to monitor said beam at a first position along the beam path.
27. The filter according to item 26, wherein said first position is after said optical waveguide.
28. The filter according to item 26 or 27, comprising a reflector for directing a fraction of the optical power of the beam into said monitoring unit.
29. The filter according to any of items 26 to 28, wherein said monitor unit measures a spectral characteristic of the beam.
30. The filter according to any of items 26 to 29, wherein said monitor unit measures the optical power in the beam.
31. The filter according to any of items 26 to 30, wherein the monitor is arranged to provide a feedback to said control unit.
32. The filter according to item 31, wherein said control unit is arranged to controlling the relative orientation of said first portion of said beam path and said angular dispersive element based on said feedback in such a manner as to stabilize said filtered broadband beam.
33. The filter according to item 32, wherein the filtered broadband beam is stabilized with respect to the spectral profile.
34. The filter according to item 32 or 33, wherein the filtered broadband beam is stabilized with respect to the optical power.
35. The filter according to any of items 32 to 34, wherein said filtered broadband beam is stabilized in less than about 1 sec, such as less than about 0.5 sec, such as less than about 0.1 sec, such as less than about 0.05 sec, such as less than about 0.01 sec, such as less than about 0.005 sec, such as less than about 0.001 sec, such as less than about 0.1 msec.
36. The filter according to any of items 1 to 35 comprising a spectral splitter arranged before the reflective element, said spectral splitter is arranged to split an incoming broadband beam into one beam with light having wavelengths in a higher wavelength range and one beam with light having wavelengths in a lower wavelength range.
37. A device for modifying an incoming broadband beam, said device comprising a first and a second filter according to any of items 1 to 35, said device comprising a spectral splitter arranged before the filters to split an incoming broadband beam into two beams of which one beam has light at wavelengths in a higher wavelength range and one beam has light at wavelengths in a lower wavelength range, one of the two beams being directed into the first filter and the other one of the two beams being directed into the second filter.
38. The device according to item 37 further comprising a spectral combiner arranged to combine the filtered beams exiting from the first and the second filters.
39. The device according to item 38, wherein said combiner comprises a dichroic mirror or a linear variable filter arranged to combine the filtered beams exiting from the first and second filters.
40. The device according to item 38, wherein said combiner comprises a wavelength division multiplexer arranged to combine the filtered beams exiting from the first and second filters.
41. The device according to any of items 37 to 40, wherein said device is arranged to filtering an incoming broadband beam to provide a signal for dual-band OCT systems.
42. A filter for filtering an incoming broadband beam modifying said beam with respect to at least a first parameter, said filter comprising
a first tunable element arranged to modify the broadband beam with respect to said first parameter;
a control unit arranged to providing a control signal to said first tunable element controlling the modification of said broadband beam on a time scale shorter than $t_1$;

43. The filter according to item 42, wherein said first tunable element comprises an element arranged to change its refractive index in response to a stimulus.
44. The filter according to item 43, wherein said stimulus is an acoustic signal or an electrical signal.
45. The filter according to item 44, wherein said stimulus is an electrical signal and said first tunable element comprises an electro-optic tunable filter.
46. The filter according to item 44, wherein said stimulus is an acoustic signal and said first tunable element comprises an acousto-optic tunable filter (AOTF).
47. The filter according to item 46, wherein said AOTF is driven by a Radio Frequency (RF) oscillator.
48. The filter according to any of items 42 to 47, comprising a second tunable element.
49. The filter according to item 48, further comprising a third tunable element and optionally a fourth tunable element.
50. The filter according to any of items 42 to 49, comprising a spectral splitter arranged before the first tunable element, said spectral splitter being arranged to split an incoming broadband beam into one beam with light having wavelengths in a higher wavelength range and one beam with light having wavelengths in a lower wavelength range.
51. The filter for filtering an incoming broadband beam modifying said beam with respect to at least a first parameter, said filter comprising
   a first tunable element arranged to at least a part of said broadband beam;
   a control unit arranged to provide a control signal to said first tunable element; and
   polarization beam splitter arranged before the first tunable element, said polarization beam splitter arranged to split a broadband beam incident on the polarization beam splitter into one beam having a first polarization and one beam having a second polarization.
52. The filter according to item 51, wherein said beam having a first polarization and said beam having a second polarization are directed into the same tunable element.
53. The filter according to item 51, wherein said beam having a first polarization being directed into one tunable element and said beam having a second polarization being directed into another tunable element.
54. The filter according to any of the claims 51 to 53 further comprising the feature(s) according to any of the claims 1 to 41.
55. The filter according to any of items 50 to 54, wherein said spectral splitter is arranged before two of said polarization splitters such that said incoming broadband beam is split into a first beam and a second beam by said spectral splitter and each of the first and the second beams subsequently are divided into two beams of different polarization, thus generating four beams.
56. The filter according to item 55, wherein the generated four beams are guided through four different tunable elements.
57. The filter according to item 56, wherein each of said four different tunable elements is controlled by one or more of said control unit.
58. The filter according to any of items 50 to 57, wherein the beams generated by splitting the incoming broadband beam are combined again after said tunable filters to provide the filtered broadband beam.
59. The filter according to item 58, wherein a polarization beam splitter is arranged to combine the split beams.
60. The filter according to any of items 51 to 59, comprising at least a first half-wave plate arranged after said polarization beam splitter to rotate the polarization of the one beam having a first polarization and/or the one beam having a second polarization.
61. The filter according to item 60, wherein said half-wave plate is arranged before a tunable element.
62. The filter according to item 60 or 61, wherein a second half wave plate is arranged after a tunable element.
63. The filter according to any of items 51 to 62, wherein said polarization beam splitter, said half-wave plate and said mirror are combined in an integrated element.
64. The filter according to any of items 48 to 63 wherein said first and second tunable elements are a first and a second AOTF, and said control unit provides a first RF signal said first AOTF and a second RF signal said second AOTF.
65. The filter according to item 64, wherein individual control of the first and second RF signals provides for a control of the polarization of the filtered beam.
66. The filter according to any of items 42 to 65, wherein said control unit comprises a Voltage Controlled Oscillator.
67. The filter according to any of items 50 to 66, wherein two beams generated either by a spectral splitter or a polarization beam splitter are guided through one tunable element.
68. The filter according to any of items 42 to 67, comprising a monitoring unit arranged to monitor said beam at a monitor position along the beam path.
69. The filter according to item 68, wherein said monitor position is after said tunable element.
70. The filter according to item 68 or 69, comprising a reflector for directing a fraction of the optical power into said monitoring unit.
71. The filter according to any of items 68 to 70, wherein said monitor unit measures a spectral characteristic of the beam.
72. The filter according to any of items 68 to 71, wherein said monitor unit provides individual measurements of the optical power at a number N of wavelengths of the beam.
73. The filter according to item 72, wherein the number N is 2 or more, such as 3, 4, 5, 6, 7, 8, 9, 10, 12, 16, 20 or more.
74. The filter according to any of items 68 to 73 wherein said monitor unit measures the optical power in the beam.
75. The filter according to any of items 68 to 74, wherein the monitor is arranged to provide a feedback to said control unit.
76. The filter according to item 75, wherein said control unit is arranged to controlling the tunable element based on said feedback in such a manner as to stabilizing the filtered beam exiting the filter.
77. The filter according to item 76, wherein the filtered beam is stabilized with respect to the spectral profile.
78. The filter according to item 76 or 77, wherein the filtered beam is stabilized with respect to the optical power in several of said N wavelengths.
79. The filter according to item 76 to 78, wherein the filtered beam is stabilized with respect to the optical power in the filtered beam.
80. The filter according to any of items 42 to 79, wherein $t_1$ is below about 10 milliseconds, such as below about 1 millisecond, such as below 0.1 milliseconds, such as below 0.01 milliseconds, such as below 0.001 milliseconds.
81. The filter according to any of items 42 to 80, wherein said first parameter is selected from the group of the spectral width, the spectral shape the optical power of the broadband beam, stability of the optical power, the polarization, the number of peaks in the broadband beam.

82. The filter according to any of items 42 to 81, wherein said tunable element filters said broadband beam such that light outside one wavelength range is suppressed, said one wavelength range having a spectra width $\Delta\lambda$ and is arranged around a central wavelength $\lambda_c$.

83. The filter according to any of item 82, wherein the spectral width $\Delta\lambda$ is below 20 nm.

84. The filter according to item 82 or 83, wherein the central wavelength $\lambda_c$ is in the range of about 400 nm to about 2600 nm.

85. The filter according to any of items item 42 to 84, wherein said control unit is arranged to provide a control signal to said tunable element which varies in time such that said central wavelength is scanned though a part of the wavelength range of said incoming broadband beam.

86. The filter according to item 85, wherein said tunable element is an AOTF and said control unit is arranged to provide a RF signal to said AOTF where the frequency of the RF signal varies in time such that said central wavelength is scanned though a part of the wavelength range of said incoming broadband beam.

87. The filter according to item 85 or 86, wherein said tunable element is an AOTF and said control unit is arranged to provide a RF signal to said AOTF where or the amplitude of the RF signal varies in time such that the spectral width varies in time.

88. The filter according to any of item 85 to 87, wherein the amplitude and frequency of the RF signal controls the wavelength and the optical power of the filtered beam from the filter, such that over a time interval $\Delta t$ light in a wavelength range exits the filter, the optical power distribution over the wavelength range having a first profile.

89. The filter according to item 88, wherein said first profile is selected from the group of a Gaussian profile, a Lorentzian profile, a Bessel profile, a Voigt profile or a super Gaussian profile.

90. The filter or device according to any of the preceding claims wherein said tunable element comprises an AOTF and VCO according to any of the attached claims.

91. A system for filtering an broadband beam, said system comprising
a broadband light source providing a broadband beam; and
a filter according to any of items 42-90, said filter being arranged to modify the beam from a said broadband light source.

92. The system according to item 91, wherein the broad band light source is selected from the group of a Supercontinuum source, a SLED, an active element based ASE source, such as an Erbium based ASE source.

93. A dual-band OCT system comprising:
a broadband light source providing a broadband beam; and
a device according to any of items 37 to 41 arranged to filter the broadband beam from said broadband light source providing a dual band signal.

94. An OCT system comprising:
a broadband light source providing a broadband beam; and
a filter according to any of items 1 to 36 and 42 to 90 arranged to filter the broadband beam from said broadband light source providing a filtered broadband beam suitable for an OCT system.

95. Use of a filter according to any of items 1 to 36 and 42 to 90 for filtering a signal from a broadband source.

96. The use according to item 95 wherein the filtered beam exiting the filter or light there from is applied as light source in a system for Optical Coherence Tomography.

97. The use according to item 95 wherein the filtered beam exiting the filter or light there from is applied as light source in a system for white-light interferometry.

98. A system for dividing a broadband beam into one or more sub-beams, said system comprising
two or more tunable elements according to any of items 48-1 to 36 and 42 to 90;
a controller arranged to control at least two of said tunable elements for separate time intervals; and
a switch for switching the control of the control unit between the two tunable elements.

99. The system according to 98, wherein said tunable elements each comprise an acousto-optic tunable filter (AOTF), said control unit comprising a RF driver and said switch comprising a RF switch.

100. The system according to 98 or 99 wherein said system further comprises a sensing unit arranged to sense which tunable element is connected to the RF driver.

101. The system according to item 100, wherein said sensing unit comprises a detector arranged to detect a DC signal.

102. A system for dividing a broadband beam into one or more sub-beams, said system comprising
two or more tunable elements according to any of items 48-90;
a controller arranged to control at least two of said tunable elements for separate time intervals; and
an RF splitter for splitting the RF signal in between the tunable elements.

Embodiments of the invention are further specified by the attached set of claims. Accordingly, embodiments of the invention further comprise a filter or device according to any of the preceding items further comprising any of the features of the attached set of claims.

The invention claimed is:

1. An optical apparatus for modifying an incoming supercontinuum beam, said apparatus comprising:
a first filter and a second filter, said device comprising a spectral splitter arranged before the filters to split an incoming supercontinuum beam into two beams of which one beam has light at wavelengths in a higher wavelength range and one beam has light at wavelengths in a lower wavelength range, one of the two beams being directed into the first filter and the other one of the two beams being directed into the second filter,
one of said first and second filters comprising:
a) beam guiding optics arranged to guide an incoming supercontinuum beam along a first portion of said beam path;
b) an angular dispersive element, consisting of a wedge or a prism, arranged so that said first portion of said supercontinuum beam is incident on a first surface of said angular dispersive element at an incident angle, whereby light at different wavelengths of the supercontinuum beam are exiting said angular dispersive element in different angles providing an angular dispersed beam;
c) a coupling lens arranged after said angular dispersive element, said lens being capable of focusing said angular dispersed beam at a first position along the beam path; and
d) an optical waveguide comprising a light guiding portion and an end facet arranged so that the light guiding portion collects at least part of the beam, where said optical waveguide is a single-mode optical fiber, wherein the beam has a larger cross sectional diameter than the cross sectional diameter of the light guiding portion such that only light in one wavelength range of said beam is collected by said light guiding portion and light at wavelengths outside said one wavelength range is filtered out to thereby produce a filtered supercontinuum beam, wherein the one wavelength range has a spectral shape with a spectral width $\Delta\lambda$ and a central wavelength $\lambda_c$, wherein said filter is tunable with respect to the central wavelength $\lambda_c$.

2. The optical apparatus according to claim 1, wherein said beam guiding optics includes a mirror arranged to guide said supercontinuum beam along said first portion of the beam path, the mirror and/or the angular dispersive element being arranged to be rotatable relative to the portion of the beam path between these elements, such that the incident angle of said first portion of said beam path relative to said angular dispersive element can be changed, whereby said central wavelength can be tuned.

3. The optical apparatus according to claim 1, wherein said optical waveguide is a microstructured endlessly single-mode optical fiber.

4. The optical apparatus according to claim 1, wherein the central wavelength of the filtered supercontinuum beam is in the range of about 700 nm to about 900 nm or in the range of about 1300 nm to about 1400 nm.

5. The optical apparatus according to claim 1, wherein the spectral shape of the filtered supercontinuum beam is selected from the group of a Gaussian profile, a Lorentzian profile, a Bessel profile, a Voigt profile and a super Gaussian profile.

6. The optical apparatus according to claim 1, further comprising:
a spatial filter element is arranged in said beam path said spatial filter being tunable for said tuning of said central wavelength $\lambda_c$.

7. The optical apparatus according to claim 1, further comprising:
a spectral combiner arranged to combine the filtered beams exiting from the first and the second filters.

8. A dual-band Optical Coherence Tomography system comprising:
a supercontinuum light source providing a supercontinuum beam; and
the optical apparatus according to claim 1, arranged to filter the supercontinuum beam from said supercontinuum light source providing a dual band signal.

9. An optical apparatus for modifying an incoming supercontinuum beam, said apparatus comprising:
a first filter and a second filter, said device comprising a spectral splitter arranged before the filters to split an incoming supercontinuum beam into two beams of which a first of said beams has light at wavelengths in a higher wavelength range and the other beam has light at wavelengths in a lower wavelength range, one of the two beams being directed into the first filter and the other one of the two beams being directed into the second filter,
one of the first and second filters comprising a tunable filter for filtering one of said beams, the one beam comprising a wavelength range of at least about 400 nm, the one beam defining a beam path through said tunable filter, said tunable filter comprising:
a) beam guiding optics;
b) a passive dispersive element comprising a wedge or a prism;
c) a tunable spatial filter; and
d) a collimating lens system comprising at least one lens;
wherein said beam guiding optics is arranged to guide the incoming supercontinuum beam along a first portion of a beam path so that a first portion of said supercontinuum beam is incident on said angular dispersive element at an incident angle, so that light at different wavelengths of the supercontinuum beam are exiting said angular dispersive element at different angles providing an angular dispersed beam, said spatial filter being arranged after the angular dispersive element.

10. The optical apparatus according to claim 1, wherein said spatial filter element is arranged in said beam path between said angular dispersive element and said coupling lens.

11. The optical apparatus of claim 9 wherein said tunable spatial filter is a mechanically tunable filter.

12. An optical apparatus for modifying an incoming supercontinuum beam, said device comprising:
a first and a second filter, said optical apparatus comprising a spectral splitter arranged before the filters to split an incoming supercontinuum beam into two beams of which one beam has light at wavelengths in a higher wavelength range and one beam has light at wavelengths in a lower wavelength range, one of the two beams being directed into the first filter and the other one of the two beams being directed into the second filter; one of said first and second filters, comprising a tunable filter for filtering a supercontinuum beam, the tunable filter having a beam path through said tunable filter, said tunable filter comprising:
a) beam guiding optics, located along the beam path;
b) a passive angular dispersive element, said passive angular dispersive element located along the beam path after said beam guiding optics and comprising a wedge, a prism or a diffractive element;
c) a tunable spatial filter located along the beam path after said passive angular dispersive element;
d) a collimating lens system comprising at least one lens, said lens located along the beam path after said tunable spatial filter;
e) an optical fiber, said optical fiber located along the beam path after said collimating lens system; and
wherein said beam guiding optics is arranged to guide a supercontinuum beam along the beam path so that said supercontinuum beam is incident on said angular dispersive element and wherein that light at different wavelengths are exiting said angular dispersive element at different angles, thereby providing an angular dispersed beam.

13. The optical apparatus of claim 12 comprising a supercontinuum light source.

14. The optical apparatus according to claim 9, further comprising:
a spectral combiner arranged to combine the filtered beams exiting from the first and the second filters.

15. The optical apparatus according to claim 9, wherein said tunable filter provides a filtered beam having a tunable central wavelength, the central wavelength of the filtered beam being in the range of about 700 nm to about 900 nm or in the range of about 1300 nm to about 1400 nm.

16. A dual-band Optical Coherence Tomography system comprising:
a supercontinuum light source providing a supercontinuum beam; and the optical apparatus according to claim 9, arranged to filter the supercontinuum beam from said supercontinuum light source providing a dual band signal.

17. The optical apparatus according to claim 12 further comprising:
 a spectral combiner arranged to combine the filtered beams exiting from the first and the second filters.

18. A dual-band Optical Coherence Tomography system comprising:
 a supercontinuum light source providing a supercontinuum beam; and
 the optical apparatus according to claim 12, arranged to filter the supercontinuum beam from said supercontinuum light source providing a dual band signal.

19. The optical apparatus according to claim 12, wherein said tunable filter provides a filtered beam having a tunable central wavelength, the central wavelength of the filtered beam being in the range of about 700 nm to about 900 nm or in the range of about 1300 nm to about 1400 nm.

* * * * *